(12) United States Patent
Hassan et al.

(10) Patent No.: US 9,766,215 B2
(45) Date of Patent: Sep. 19, 2017

(54) ANALYTICAL SYSTEM AND METHOD FOR DETECTING VOLATILE ORGANIC COMPOUNDS IN WATER

(75) Inventors: Kazi Z. A. Hassan, Huntsville, AL (US); William M. Cost, Hartselle, AL (US); John Arthur Morse, Owens Cross Roads, AL (US); Michael L. Doutt, Madison, AL (US); Glenn Stacey Geis, Huntsville, AL (US)

(73) Assignee: Parker-Hannifin Corporation, Cleveland, OH (US)

( * ) Notice: Subject to any disclaimer, the term of this patent is extended or adjusted under 35 U.S.C. 154(b) by 573 days.

(21) Appl. No.: 14/343,138

(22) PCT Filed: Sep. 7, 2012

(86) PCT No.: PCT/US2012/054144
§ 371 (c)(1),
(2), (4) Date: Apr. 4, 2014

(87) PCT Pub. No.: WO2013/036760
PCT Pub. Date: Mar. 14, 2013

(65) Prior Publication Data
US 2015/0143872 A1    May 28, 2015

Related U.S. Application Data

(60) Provisional application No. 61/531,974, filed on Sep. 7, 2011.

(51) Int. Cl.
*G01N 30/76* (2006.01)
*G01N 29/02* (2006.01)
(Continued)

(52) U.S. Cl.
CPC .............. *G01N 30/76* (2013.01); *G01N 1/10* (2013.01); *G01N 1/4055* (2013.01);
(Continued)

(58) Field of Classification Search
CPC .................................................. G01N 29/024
See application file for complete search history.

(56) References Cited

U.S. PATENT DOCUMENTS

| 4,230,464 A | 10/1980 | Bonmati et al. |
| 4,895,017 A | 1/1990 | Pyke et al. |

(Continued)

FOREIGN PATENT DOCUMENTS

| DE | 2732762 | 3/1979 |
| GB | 2279740 | 1/1995 |

(Continued)

OTHER PUBLICATIONS

PCT/US2012/054144; PCT International Search Report and Written Opinion of the International Searching Authority mailed Feb. 14, 2013.

(Continued)

*Primary Examiner* — Paul West
*Assistant Examiner* — Mark A Shabman
(74) *Attorney, Agent, or Firm* — Renner, Otto, Boisselle & Sklar, LLP

(57) ABSTRACT

An analytical system and method for detecting volatile organic chemicals in water including a coated SAW detector that provides for improved reduction of moisture at the coating of the SAW detector. A stabilized SAW sensitivity and long lasting calibration is achieved. The analytical system further includes an improved sample vessel and sparger that allow for easy grab sample analysis, while also providing efficient purging of the volatile organic compounds from the water sample. In addition, an improved preconcentrator provides a stabilized sorbent bed.

15 Claims, 20 Drawing Sheets

(51) Int. Cl.
*G01N 1/10* (2006.01)
*G01N 1/40* (2006.01)
*G01N 30/02* (2006.01)

(52) U.S. Cl.
CPC ... *G01N 29/022* (2013.01); *G01N 2001/4066* (2013.01); *G01N 2030/025* (2013.01); *G01N 2291/021* (2013.01)

(56) References Cited

U.S. PATENT DOCUMENTS

| | | |
|---|---|---|
| 5,151,110 A | 9/1992 | Bein et al. |
| 5,258,171 A | 11/1993 | Eltomi |
| 5,289,715 A * | 3/1994 | Staples ............... G01N 29/024 73/24.01 |
| 5,426,300 A | 6/1995 | Voss et al. |
| 5,492,838 A | 2/1996 | Pawliszyn |
| 5,625,139 A | 4/1997 | Stormbom |
| 5,880,552 A | 3/1999 | McGill et al. |
| 5,917,135 A | 6/1999 | Michaels et al. |
| 5,920,143 A | 7/1999 | Tarui et al. |
| 6,074,461 A | 6/2000 | Wilson |
| 6,085,576 A | 7/2000 | Sunshine et al. |
| 6,134,944 A | 10/2000 | Yu et al. |
| 6,234,006 B1 | 5/2001 | Sunshine et al. |
| 6,244,096 B1 | 6/2001 | Lewis et al. |
| 6,295,861 B1 | 10/2001 | Tom et al. |
| 6,319,724 B1 | 11/2001 | Lewis et al. |
| 6,387,329 B1 | 5/2002 | Lewis et al. |
| 6,418,783 B2 | 7/2002 | Sunshine et al. |
| 6,422,061 B1 | 7/2002 | Sunshine et al. |
| 6,455,319 B1 | 9/2002 | Lewis et al. |
| 6,467,333 B2 | 10/2002 | Lewis et al. |
| 6,566,983 B2 | 5/2003 | Shin |
| 6,610,367 B2 | 8/2003 | Lewis et al. |
| 6,631,333 B1 | 10/2003 | Lewis et al. |
| 6,658,915 B2 | 12/2003 | Sunshine et al. |
| 6,684,683 B2 | 2/2004 | Potyrailo et al. |
| 6,691,702 B2 | 2/2004 | Appel et al. |
| 6,703,241 B1 | 3/2004 | Sunshine et al. |
| 6,759,010 B2 | 7/2004 | Lewis et al. |
| 6,772,513 B1 | 8/2004 | Frye-Mason et al. |
| 6,837,095 B2 | 1/2005 | Nakayama et al. |
| 6,841,391 B2 | 1/2005 | Lewis et al. |
| 6,870,234 B2 | 3/2005 | Brewer et al. |
| 6,883,364 B2 | 4/2005 | Sunshine et al. |
| 6,890,715 B1 | 5/2005 | Lewis et al. |
| 6,914,220 B2 | 7/2005 | Tian et al. |
| 6,914,279 B2 | 7/2005 | Lu et al. |
| 6,962,675 B2 | 11/2005 | Lewis et al. |
| 6,981,947 B2 | 1/2006 | Melker |
| 7,047,792 B1 | 5/2006 | Bhethanabotla et al. |
| 7,052,468 B2 | 5/2006 | Melker et al. |
| 7,052,854 B2 | 5/2006 | Melker et al. |
| 7,066,985 B2 | 6/2006 | Deane et al. |
| 7,078,237 B1 | 7/2006 | Mowry et al. |
| 7,089,780 B2 | 8/2006 | Sunshine et al. |
| 7,104,963 B2 | 9/2006 | Melker et al. |
| 7,122,152 B2 | 10/2006 | Lewis et al. |
| 7,135,059 B2 | 11/2006 | Deane et al. |
| 7,141,446 B2 | 11/2006 | Brewer et al. |
| 7,144,553 B2 | 12/2006 | Lewis et al. |
| 7,147,695 B2 | 12/2006 | Mitra |
| 7,153,272 B2 | 12/2006 | Talton |
| 7,168,298 B1 | 1/2007 | Manginell et al. |
| 7,189,353 B2 | 3/2007 | Lewis et al. |
| 7,194,891 B2 | 3/2007 | Tuller et al. |
| 7,282,676 B1 | 10/2007 | Bouchier et al. |
| 7,299,711 B1 | 11/2007 | Linker et al. |
| 7,399,449 B1 | 7/2008 | Oborny et al. |
| 7,430,928 B2 | 10/2008 | Grate et al. |
| 2002/0073764 A1 | 6/2002 | Guerra et al. |
| 2003/0115770 A1* | 6/2003 | Harano ............ H01L 21/31116 34/266 |
| 2005/0226773 A1 | 10/2005 | Liu |
| 2005/0289351 A1 | 12/2005 | England et al. |
| 2006/0088445 A1 | 4/2006 | Lewis et al. |
| 2006/0130611 A1 | 6/2006 | Lynn |
| 2006/0210425 A1 | 9/2006 | Mirkarimi |
| 2007/0062255 A1 | 3/2007 | Talton |
| 2007/0085446 A1 | 4/2007 | Chen |
| 2008/0289397 A1 | 11/2008 | Hassan et al. |
| 2010/0018288 A1* | 1/2010 | Yamanaka .......... G01N 29/022 73/24.02 |
| 2010/0180667 A1 | 7/2010 | Bender et al. |

FOREIGN PATENT DOCUMENTS

| | | |
|---|---|---|
| JP | 2234507 | 9/1990 |
| WO | 9631773 | 10/1996 |
| WO | 2005066288 | 7/2005 |

OTHER PUBLICATIONS

PCT/US2012/054144; PCT International Preliminary Report on Patentability mailed Sep. 4, 2013.

Lu, Chia-Jung et al. "A Dual-Adsorbent Preconcentrator for a Portable Indoor-VOC Microsensor System", Anal. Chem., vol. 73, No. 14, Jul. 15, 2001, pp. 3449-3457.

Siegal, M.P. et al., "Nannporous Carbon Films for Gas Microsensors", Langmuir, vol. 20, 2004, pp. 1194-1198.

Groves, W.A. et al., "Analyzing Organic Vapors in Exhaled Breath Using a Surface Acoustic Wave Sensor Array with Preconcentration: Selection and Characterization of the Preconcentrator Adsorbent", Analytica Chimica Acta, vol. 371, 1998, pp. 131-143.

Matney, M.L. et al., "Multisorbent Tubes for Collecting Volatile Organic Compounds in Spacecraft Air", AIHAJ, vol. 61, Jan./Feb. 2000, pp. 69-75.

M.P. Siegal et al., "Nanoporous-Carbon Adsorbers for Chemical Microsensors," Sandia Report, SAND2004-5277, Nov. 2004, 35 pages.

M.P. Siegal and W.G. Yelton, "Nanoporous-Carbon Coatings for Gas-Phase Chemical Microsensors," Advances in Science and Technology, vol. 48, 2006, pp. 161-168.

M.P. Siegal et al., "Nanoporous-carbon films for microsensor preconcentrators," Appl. Phys. Lett., vol. 80, No. 21, May 27, 2002, pp. 3940-3942.

Curtis D. Mowry et al., "Real-time Discriminatory Sensors for Water Contamination Events: LDRD 52595 Final Report," Oct. 2005, 57 pages.

Curtis D. Mowry et al., "Recent Advancements Toward Field Portable Detection of THMs by Surface Acoustic wave Detection," Mar. 2007, 27 pages.

Curtis D. Mowry et al., "Portable Field System for Rapid, On-Site Detection of Disinfection Byproducts in Water," Nov. 2005, 26 pages.

Tenax TA Adsorbent Resin Physical Properties, accessed Apr. 8, 2008, http://www.sisweb.com/index/referenc/tenaxtam.htrn, 3 pages.

Inficon Hapsite Situprobe, 2007, 2 pages.

C. Eric Boswell, "Fast and Efficient Volatiles Analysis by Purge and Trap GC/MS," 1999, 5 pages.

Surface acoustic wave, accessed Apr. 8, 2008, http://en.wikipedia.org/wiki/Surface_acoustic_wave, 2 pages.

Acoustic Wave Technology Sensors, Drafts, Oct. 2000 http://www.sensorsmag.com/articles/1000/68/main.shtml, 13 pages.

* cited by examiner

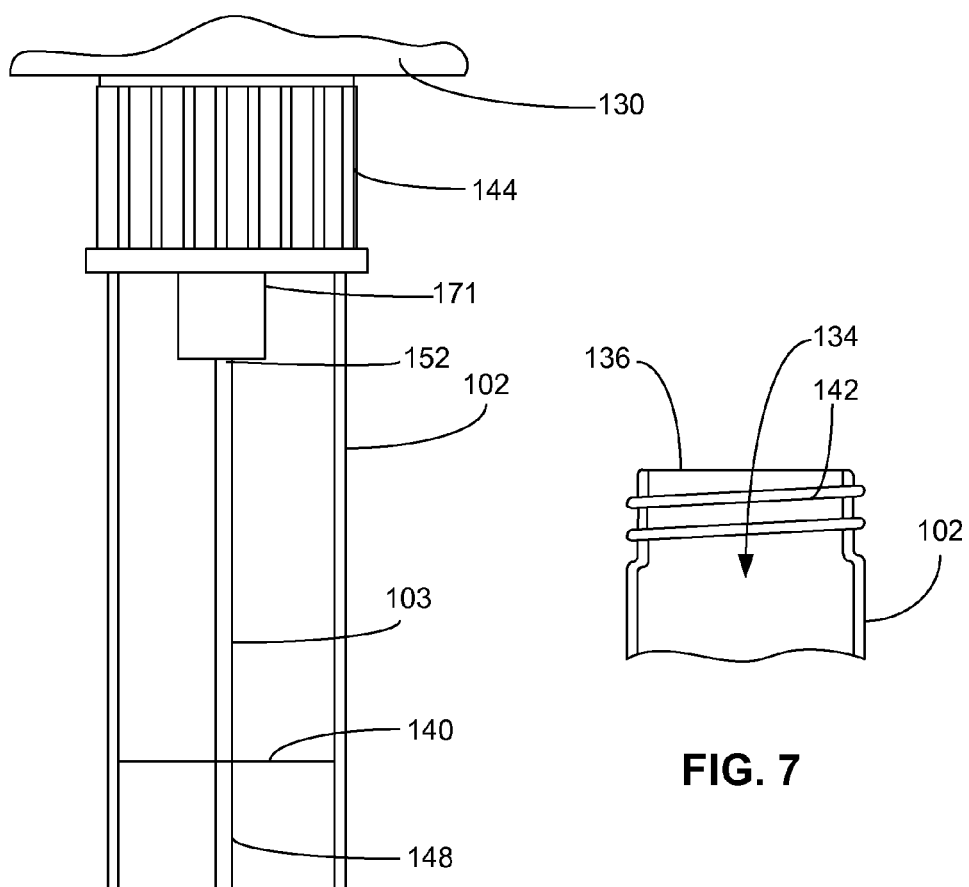
FIG. 6
FIG. 7
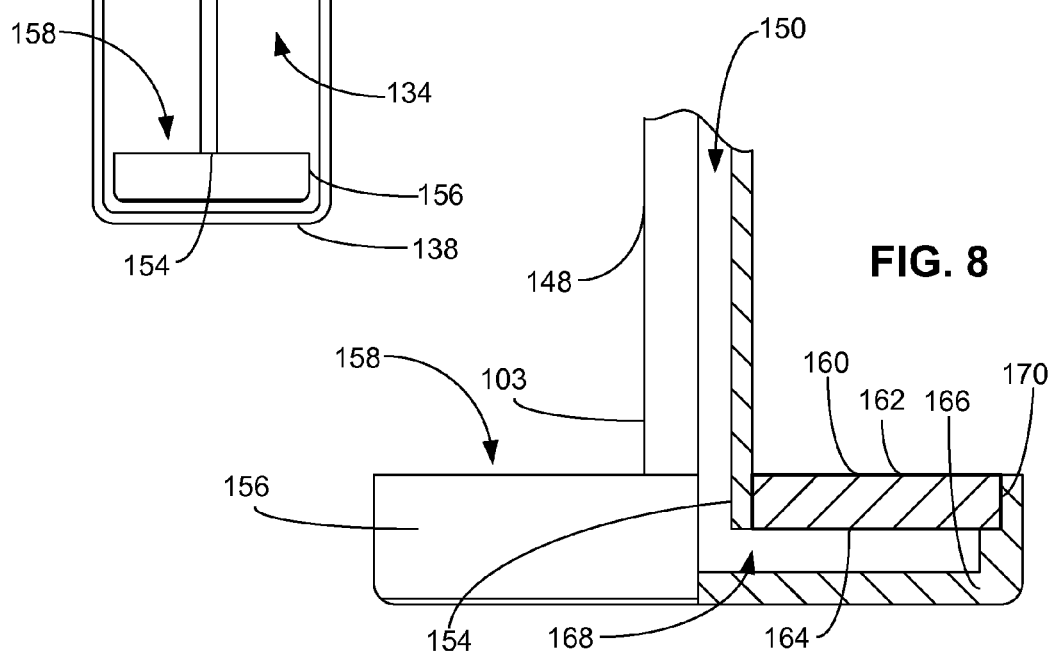
FIG. 8

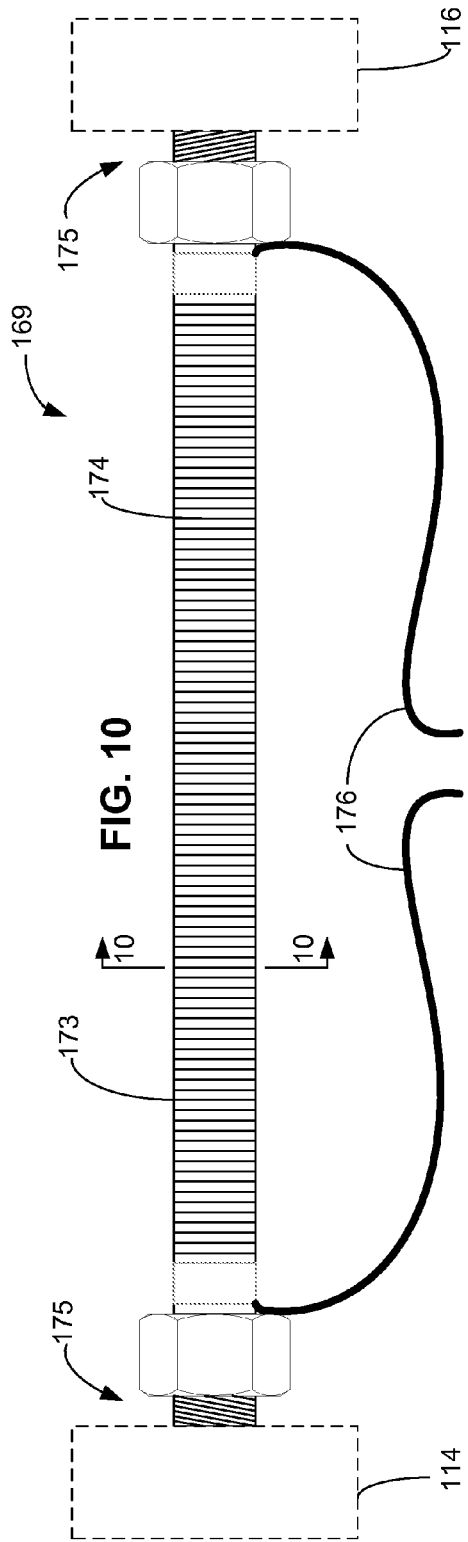
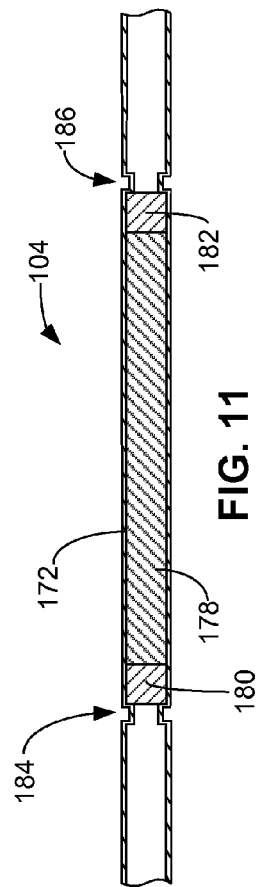
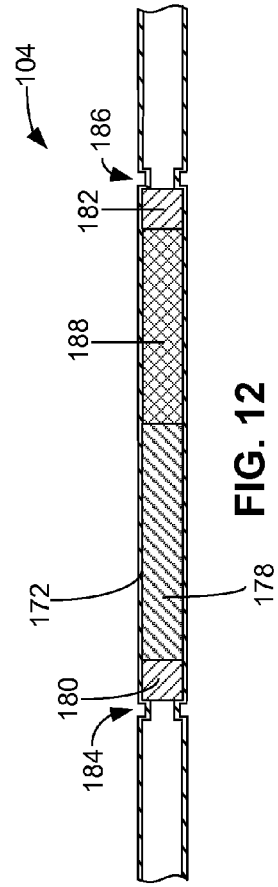
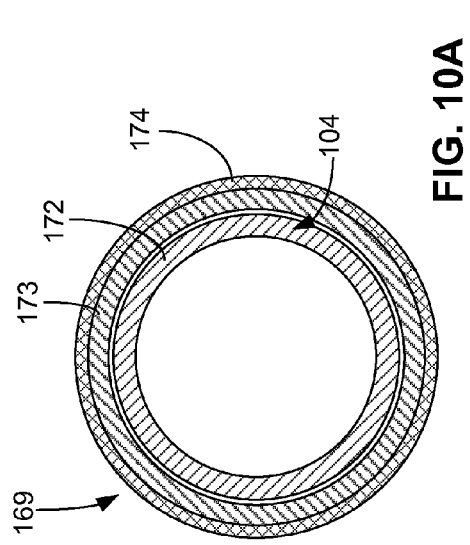

ANALYTICAL SYSTEM AND METHOD FOR DETECTING VOLATILE ORGANIC COMPOUNDS IN WATER

RELATED APPLICATIONS

This application is a national phase of International Application No. PCT/US2012/054144 filed Sep. 7, 2012 and published in the English language and which claims the benefit of U.S. Provisional Application No. 61/531,974 filed Sep. 7, 2011, the disclosures of which are incorporated herein by reference in their entireties.

FIELD OF INVENTION

The present invention relates to chemical analysis systems and methods, and in particular to an analytical system and method for detecting volatile organic compounds in water.

BACKGROUND

Purge and trap is a well known technique for the extraction of volatile organic chemicals (VOCs) out of liquids (including water). In a typical laboratory method, an inert carrier gas, often helium, is used to transfer VOCs from the liquid phase to the gas phase. Typically, a U-shaped glass tube sparger vessel is utilized to flow pressurized carrier gas up from the bottom of a blown glass vessel through a porous frit. This U-shaped glass tube sparger vessel is typically fixed in place and does not allow for easy grab sample analysis.

Once in the gas phase, the VOCs are transferred to a trap such as an adsorbent bed or liquid nitrogen cold trap. Preconcentrators (also referred to as traps) are typically used to adsorb VOCs to promote analysis using a gas chromatograph (GC) column, mass spectrometers or other analytical instrument technologies. Preconcentrators typically include one or more adsorbent materials loosely packed within stainless steel or glass tubes. The carrier gas containing the VOCs passes through the length of the tube body and deposits the volatile organics onto the adsorbent material. After a predetermined period, the preconcentrator is rapidly heated and carrier gas is introduced to transfer the VOCs to analytical instrumentation (e.g. a GC column via an injection valve operation).

Analysis of the VOCs may be performed by a surface acoustic wave (SAW) detector-based system, which detects the mass of the VOCs by the change of frequency of the SAW detector. It has been proposed to coat the SAW detector with a suitable polymer or nanoporous carbon (NPC) coating to enhance the detection of VOCs (e.g. trihalomethane (THM) chemical compounds).

SUMMARY OF INVENTION

The present invention provides improvements in chemical analysis systems and methods and, in particular, improvements in the reduction and management of moisture (e.g. water content) present at the coating of the SAW detector.

In purge and trap systems, the presence of a high concentration of moisture in the system is very common because the VOCs are sparged from a volume of water. Moisture is consequently introduced to the SAW detector and is retained in the SAW coating after repeated exposure. Polymer coated SAW detectors are subject to a reduction in sensitivity (and possibly degradation) upon exposure to moisture (water). And while NPC coatings generally provide for improved sensitivity over polymer coatings for the THM chemical compounds of interest at parts per billion (ppb) levels, NPC coated SAW detectors are also not immune from problems created by moisture exposure.

Moisture increases the overall mass of the SAW coating which then reduces the sensitivity (or electrical signal strength) in two ways. Firstly, the water molecules occupy active sites for analyte adsorption. This means less of the total analyte mass that is exhausted from the GC column is adsorbed on the SAW coating. Less mass adsorbed results in less frequency change, lower electrical signal, and lower calculated concentration. Secondly, the overall mass of the SAW coating is increased such that the adsorbed analyte is a smaller percentage of overall coating mass. This results in a smaller frequency shift which results in a lower calculated concentration than actually present.

As a result of this degradation in sensitivity, recalibration of the system must be performed more frequently, which is time consuming and expensive. Furthermore, continued degradation of sensitivity and signal strength results in the eventual loss of the ability to accurately measure the VOCs at low ppb levels, regardless of calibration.

The sensitivity of the SAW detector may be restored by heating the SAW coating at high temperature to remove moisture from the SAW coating. This can improve sensitivity dramatically (e.g. a 3×-4× improvement) because of the significant increase in active sites and the reduced mass of the SAW coating. However, sensitivity of the SAW detector will quickly degrade (e.g. about 50%) over a few detection processes as moisture is retained in the SAW coating, making the calibration of the SAW detector problematic. In such a system, a heater would likely have to regenerate the SAW coating after every detection process to maintain calibration accuracy. This would add substantial time to the process (waiting for heat up and cool down), as well as cost and complexity to the system. In addition, the signal peaks for heavier compounds, such as bromoform, widen substantially (desorption slows) and peak tailing effect becomes prominent on a newly regenerated SAW detector. This is not acceptable chromatography, as only symmetrical, narrow and tall peaks are desired.

The present invention provides improvements in the reduction and the management of moisture (e.g. water content) at the coating of the SAW detector. Features of the present invention provide for improved and stabilized sensitivity of the SAW detector. In addition, an improved sample vessel and sparger allow for easy grab sample analysis, while also providing efficient purging of the VOCs from the water sample. An improved preconcentrator is also provided. These improvements may be employed individually or collectively in a system that purges the VOCs (e.g., one or more THM chemical compounds of interest) from a sample (e.g. water sample by bubbling a carrier gas through the sample), collects (e.g. traps) the purged chemicals in a preconcentrator, separates the chemicals temporally as through use of a GC column, and detects the chemicals using a SAW detector.

Accordingly, a system for detecting organic compounds in water includes a surface acoustic wave detector configured to detect a mass of organic compounds separated by a gas chromatograph column, the surface acoustic wave detector having a sensing surface with a coating; a vacuum pump for lowering pressure at the coating of the surface acoustic wave detector; and a controller configured to control operation of the vacuum pump to lower pressure at the coating of the surface acoustic wave detector to remove moisture from the coating.

According to another aspect of the invention, a method for detecting organic compounds in water includes purging the organic compounds from a water sample contained in a sample vessel; collecting the organic compounds with a preconcentrator; desorbing the organic compounds from the preconcentrator; separating the organic compounds as desorbed from the preconcentrator with a gas chromatograph column; detecting the mass of organic compounds separated by a gas chromatograph column with the acoustic wave detector; and lowering pressure at a coating of the surface acoustic wave detector to remove moisture from the coating.

According to another aspect of the invention, a method is provided for reducing water content of a coating of a surface acoustic wave detector configured to detect a mass of organic compounds separated by a gas chromatograph column, the surface acoustic wave detector having a sensing surface with a coating, the method including lowering pressure at the coating of the surface acoustic wave detector to remove moisture from the coating.

According to another aspect of the invention, a system for detecting organic compounds in water includes a preconcentrator configured to collect the organic compounds; a gas chromatograph column configured to separate the organic compounds as desorbed from the preconcentrator; a surface acoustic wave detector configured to detect the mass of the organic compounds separated by the gas chromatograph; a housing that houses the preconcentrator, the gas chromatograph column, and the surface acoustic wave detector; and a sample vessel removably attached to the housing configured to contain a water sample from which the organic compounds are purged.

According to another aspect of the invention, a sparger includes a tubular member configured as an open-ended hollow body surrounding an internal volume and defining a longitudinal axis, the tubular member having a top end and a bottom end; a porous member mounted to the bottom end, the porous member including a top major surface and a bottom major surface respectively facing in opposite longitudinal directions along the longitudinal axis of the tubular member; and a cap mounted to the porous member and forming with the porous member a volume extending over a major extent of the bottom major surface and communicating with the internal volume of the tubular member.

According to another aspect of the invention, a preconcentrator for collecting organic compounds purged from a water sample includes a tubular member; a sorbent bed disposed in the tubular member; and first and second porous retaining members disposed in the tubular member at opposite ends of the sorbent bed for retaining the sorbent bed, wherein the first and second porous retaining members are constrained against movement by respective inwardly crimped portions of the tubular member.

The foregoing and other features of the invention are hereinafter described in greater detail with reference to the accompanying drawings.

BRIEF DESCRIPTION OF THE DRAWINGS

FIG. 6 is a side view of an exemplary sample vessel and sparger used in the system;

FIG. 7 is a side view of parts of the exemplary sample vessel used in the system;

FIG. 8 is a partial cross-sectional view of parts of the exemplary sparger used in the system;

FIG. 10 is a depiction of an exemplary preconcentrator housing assembly used in the system;

FIG. 10A is a partial cross-sectional view of parts of the exemplary preconcentrator and preconcentrator housing assembly used in the system, taken along line 10-10 of FIG. 10;

FIG. 11 is a cross-sectional view of parts of the exemplary preconcentrator used in the system;

FIG. 12 is a cross-sectional view of parts of another exemplary preconcentrator used in the system;

DETAILED DESCRIPTION

Figure 1:
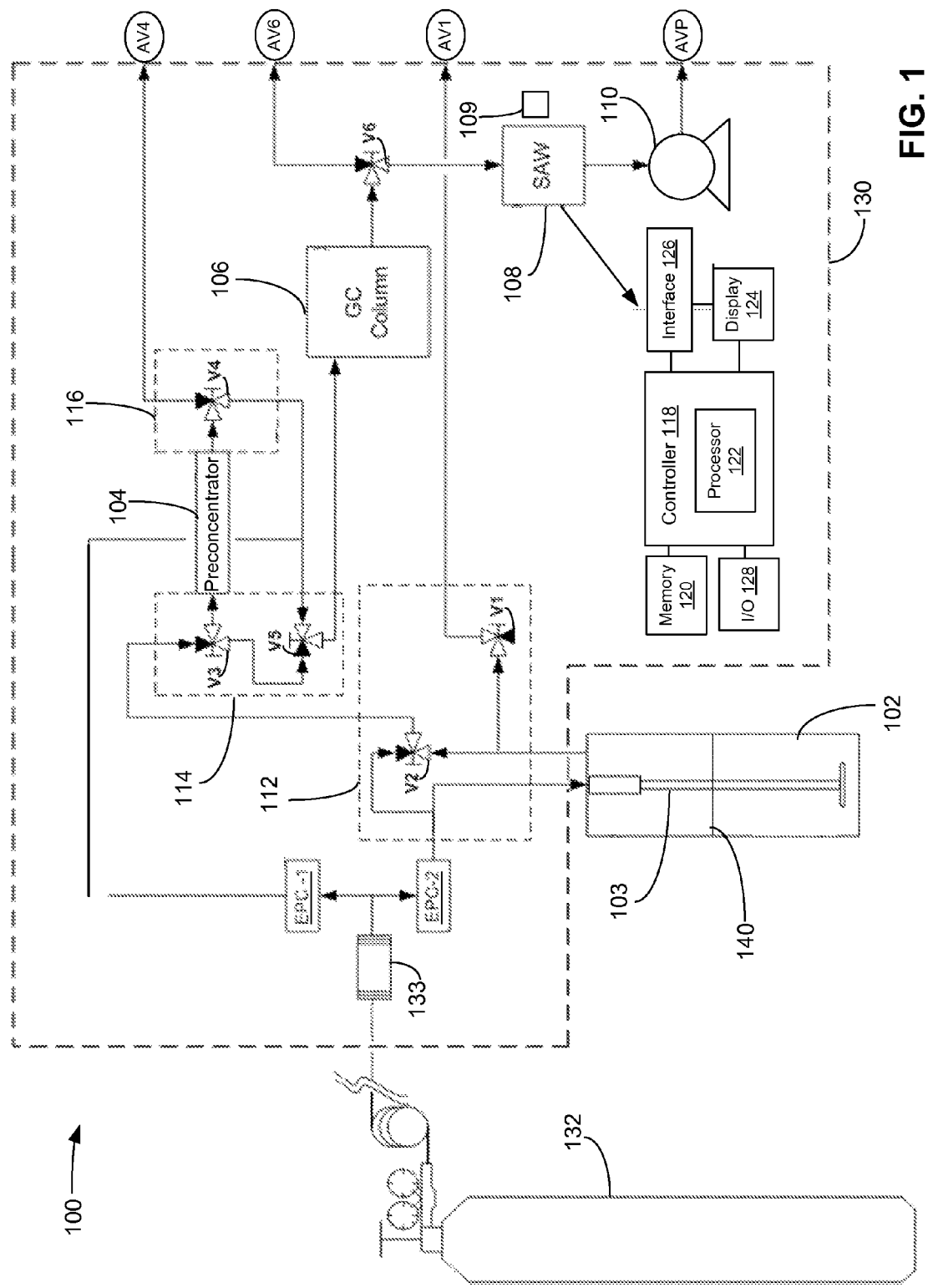
FIG. 1 is a schematic illustration of an exemplary chemical analysis system according to the invention in a standby state.
Figure 2:
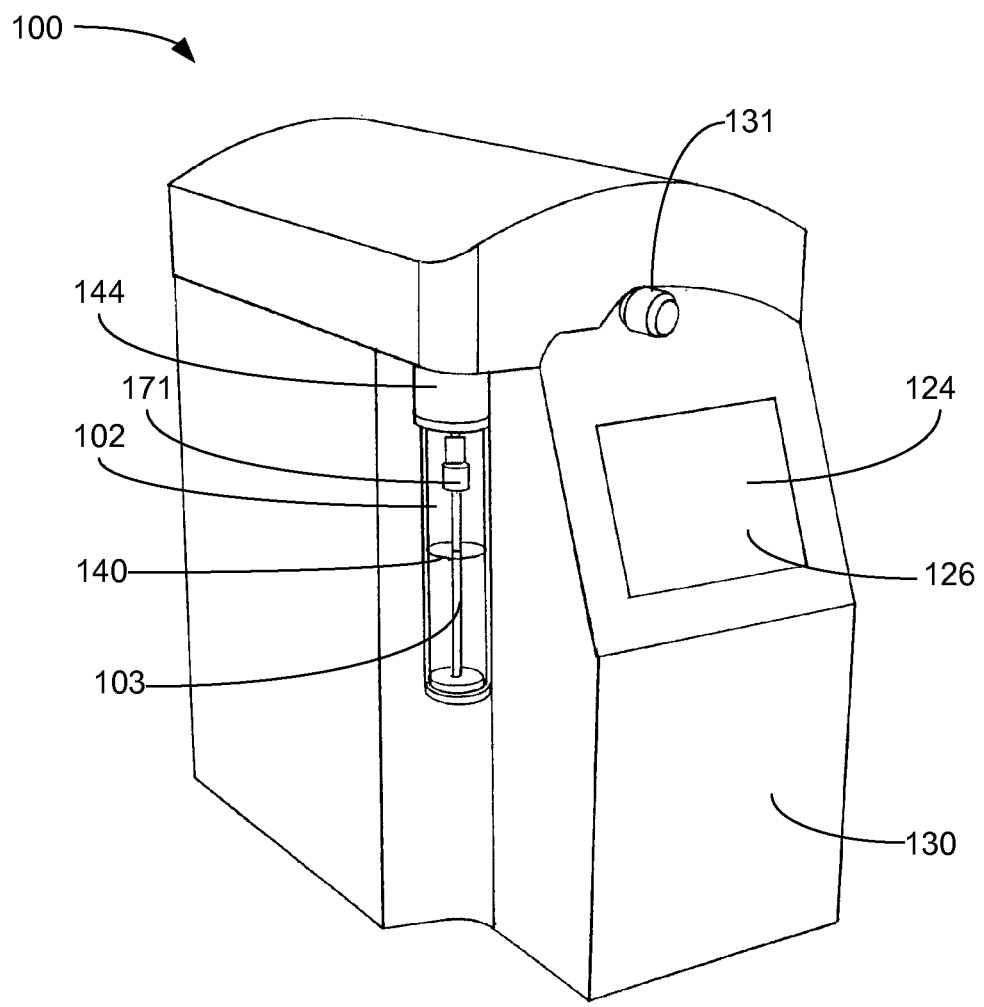
FIG. 2 is a depiction of an exemplary chemical analysis system according to the invention.

Referring now to the drawings in detail and initially to FIGS. 1 and 2, an exemplary chemical analysis system according to the invention is indicated generally by reference numeral 100. The system 100 generally includes a sample vessel 102, a sparger 103, a preconcentrator 104, a GC column 106, a SAW detector 108, and a vacuum pump 110.

The illustrated system 100 has particular application as a system for detecting THM chemical compounds in water and will be chiefly described in this context. In one example, the system 100 is suitable for drinking water analysis of THM chemical compounds at low ppb levels. It should be understood, however, that this is exemplary and a system according to the invention may have other applications as well, such as other organic compounds typically with molecular weights lower than 4000 Daltons.

The sample vessel 102, sparger 103, preconcentrator 104, GC column 106, SAW detector 108, and a vacuum pump 110 may be in fluid communication via flow paths through the system, such as via conduits, tubes, and the like. The system includes a sparger manifold 112, a GC manifold 114, a preconcentrator (PC) manifold 116, and a control valve V6. The sparger manifold 112 is in fluid communication with the sparger 103 and the sample vessel 102 and includes control valves V1 and V2. The control valve V1 may be operated to provide a flow path from the sparger manifold 112 to vent AV1. The control valve V2 may be operated to provide a flow path from the sparger manifold 112 to the GC manifold 114. The GC manifold 114 is in fluid communication with the preconcentrator 104 and the GC column 106 and includes control valves V3 and V5. The control valve V3 may be operated to provide a flow path from the sparger manifold 112 to the GC manifold 114, and may be operated to provide a flow path from the GC manifold 114 to the preconcentrator 104. The control valve V5 may be operated to provide a flow path from the GC manifold 114 to the PC manifold 116, and may be operated to provide a flow path from the GC manifold 114 to the GC column 106. The PC manifold 116 is in fluid communication with the preconcentrator 104 and includes control valve V4. The control valve V4 may be operated to provide a flow path from the PC manifold 116 to vent AV4, and may be operated to provide a flow path from the PC manifold 116 to the preconcentrator 104. The control valve V6 may be operated to provide a flow path from the GC column 106 to the SAW detector 108 or the vent AV6.

The system 100 further includes a controller 118 for controlling the functions and overall operation of the system 100 (e.g. operation of valves, signal processing, heating, data collection from the detector, data analysis, output of data, etc). The functions and overall operation may be provided by one or more programs stored in a non-transitory computer readable medium (e.g. memory 120) and executed by a processor 122 of the controller 118. A display 124 may be coupled to the controller 118 for presenting information to a user (e.g. analysis data). A user interface 126 may also be included that allows the user to interact with the system 100. The display 124 and the user interface 126 may be used in conjunction with one another to implement a touch screen associated with the display 124 (e.g. as shown in FIG. 2). One or more input/output (I/O) interface(s) 128, such as a USB interface, may couple the controller 118 to another device (e.g., a computer) or an accessory (e.g., a printer) via a cable.

The preconcentrator 104, GC column 106, SAW detector 108, and vacuum pump 110, may be housed within the system housing 130. The sample vessel 102 may be removably attached to the housing 130. The sparger 103 extends from the housing 130 and is arranged such that the sparger 103 would be disposed in the sample vessel 102 when the sample vessel 102 is attached to the housing 130. The preconcentrator 104 may also be removed from the housing and system via access port 131 (e.g., as shown in FIG. 2).

A gas supply 132 is coupled to the system 100 for supplying carrier gas to the system 100. The carrier gas may be any suitable carrier gas, for example, an inert gas or air. Some exemplary carrier gases may include helium, nitrogen, argon, hydrogen, and/or air. Carrier gas may be supplied to the system 100 under pressure and may pass through a filter 133 for removal of moisture and other contaminates from the carrier gas stream. The pressure of the carrier gas may be regulated via electronic pressure controllers EPC-1 and EPC-2.

The various components of the system 100 are discussed in more detail below.

Figure 3:
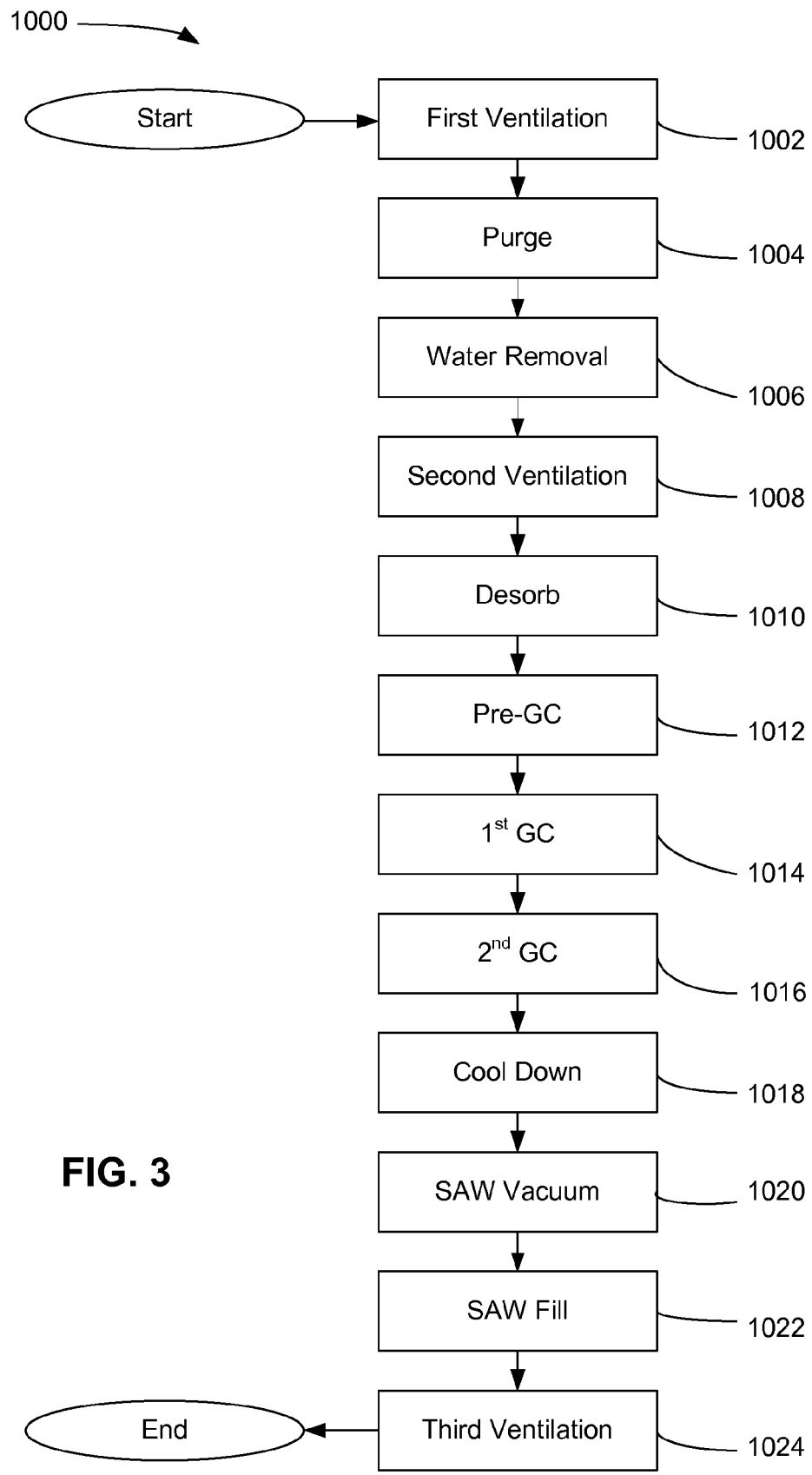
FIG. 3 is a schematic flow diagram of an exemplary analytical process performed by the exemplary chemical analysis system.

With additional reference to FIG. 3, the system 100 may be controlled by the controller 118 to perform an analytical process 1000 for detecting THM chemical compounds in water. In accordance with the exemplary analytical process 1000 shown in FIG. 3, one or more THM chemical compounds of interest may be purged from a water sample contained in the sample vessel 102, collected in a preconcentrator 104, desorbed from the preconcentrator 104, separated via the GC column 106, and detected using the SAW detector 108.

As described below, the system 100 includes various features that prevent sensitivity decay of the SAW detector 108 due to exposure of the SAW coating to moisture by minimizing moisture exposure to the SAW coating. These features include, for example, added headspace to the sample vessel 102 to minimize moisture penetration into the preconcentrator, a water removal process to exhaust moisture from the preconcentrator 104 prior to desorption of the THM chemical compounds into the GC column 106, the use of a hydrophobic adsorbent in the preconcentrator 104 (e.g. Tenax™ TA), and a pre-GC process in which the initial moisture-laden column effluent gas stream from the GC column is vented from the system. However, moisture may not be completely removed from the gas stream and moisture may inevitably come into contact with the SAW coating.

The inventors have achieved a SAW detector 108 having stabilized sensitivity and long lasting calibration by applying a vacuum to the SAW coating to remove a portion of the moisture embedded in the SAW coating. The vacuum pump 110 may be controlled so that the pressure at the SAW coating of the SAW detector 108 is lowered, e.g. to about the vapor pressure of water. In some embodiments, this is performed at a constant temperature (e.g. the pressure at the coating is lowered without application of heat at the coating). Although in other embodiments, heat may be applied to the SAW coating (e.g. via a heating member 109) to increase the vapor pressure of the moisture embedded in the SAW coating. The lowered pressure aids in the release (evaporation) of moisture embedded in the SAW coating that otherwise would not be released simply by passing carrier gas across the SAW coating. In some embodiments, a vacuum is applied to the SAW coating without the flow of carrier gas at the SAW coating. In other embodiments, the carrier gas is flowed across the SAW coating while the SAW coating is under vacuum.

Generally only a portion of the moisture embedded in the SAW coating (e.g. the lightly embedded moisture at the NPC coating) is removed from the SAW coating. This avoids a dramatic increase of sensitivity (necessitating calibration), as well as the dramatic degradation associated therewith. In addition, desorption of heavier compounds at the SAW detector, such as bromoform, is not slowed (and peak tailing effects are minimized). It has been found by the inventors that the sensitivity of the SAW detector subjected to this vacuum maintains the sufficient sensitivity for detection of THM chemical compounds at low ppb levels. Furthermore, the application of the vacuum consistently removes the lightly embedded moisture and allows the active surface concentration on the SAW to be consistently restored to about the same level. The vacuum process may be performed at one or more times during the analytical process 1000, thereby providing a stable SAW sensitivity that produces acceptable chromatography peaks. As a result, SAW calibration can be long lasting.

Features of the present invention are described below in relation to the exemplary analytical process 1000. Although the flow chart of FIG. 3 shows a specific order of the steps of the analytical process 1000, such order may be changed relative to the order shown. Also, one or more of the steps shown in the flow chart may be omitted.

Prior to the start of the analytical process 1000, the system 100 may be in a standby state, e.g. as shown in FIG. 1. A water sample may be collected using the removable sample vessel 102, and the sample vessel 102 may be attached to the housing 130 for analysis of the water sample.

Figure 4:
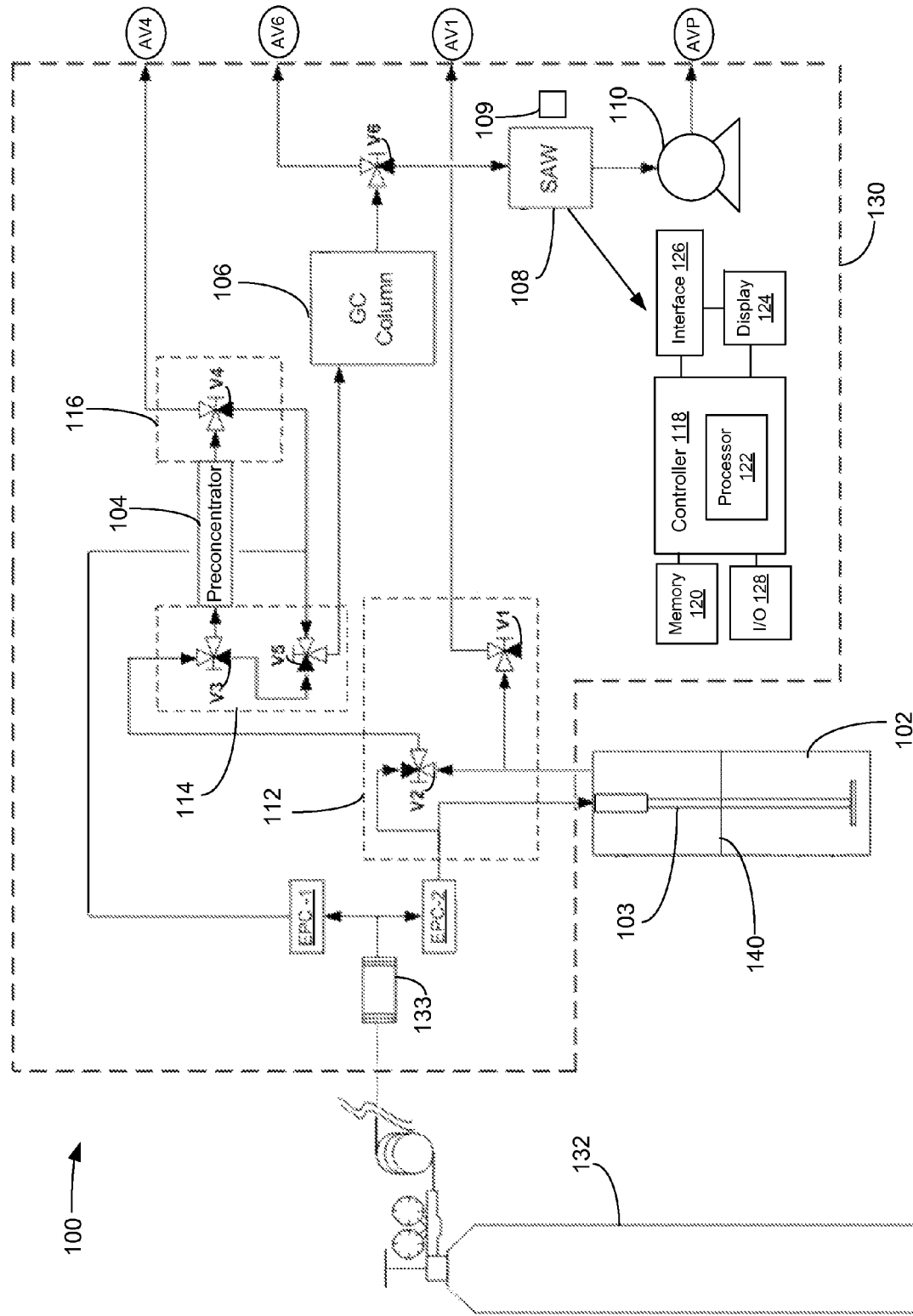
FIG. 4 is a schematic illustration of an exemplary chemical analysis system according to the invention in a first ventilation state.

At step 1002, the system 100 is operated via the controller 118 to be in a first ventilation state and the system 100 undergoes a first ventilation process. The duration of the first ventilation process may range from about 0 seconds to about 10 seconds. In one embodiment, the first ventilation process is performed for about 5 seconds. FIG. 4 shows the system 100 in the first ventilation state. The electronic pressure controllers EPC-1 and EPC-2 are controlled via controller 118 such that there is no flow of carrier gas through the system 100, and the control valves V1-V6 are controlled via the controller 118 such that built up pressure present in the system may be released. Control valve V1 is operated to provide a flow path from the sparger 103 and the sample vessel 102 to vent AV1. Control valves V2, V3, and V4 are operated to provide a flow path from the sparger 103, sample vessel 102, and preconcentrator 104 to vent AV4. Control Valves V5 and V6 are operated to provide a flow path from the GC column 106 to vent AV6. The vacuum pump is also operated and provides a flow path from the SAW detector 108 to vent AVP.

Figure 5:
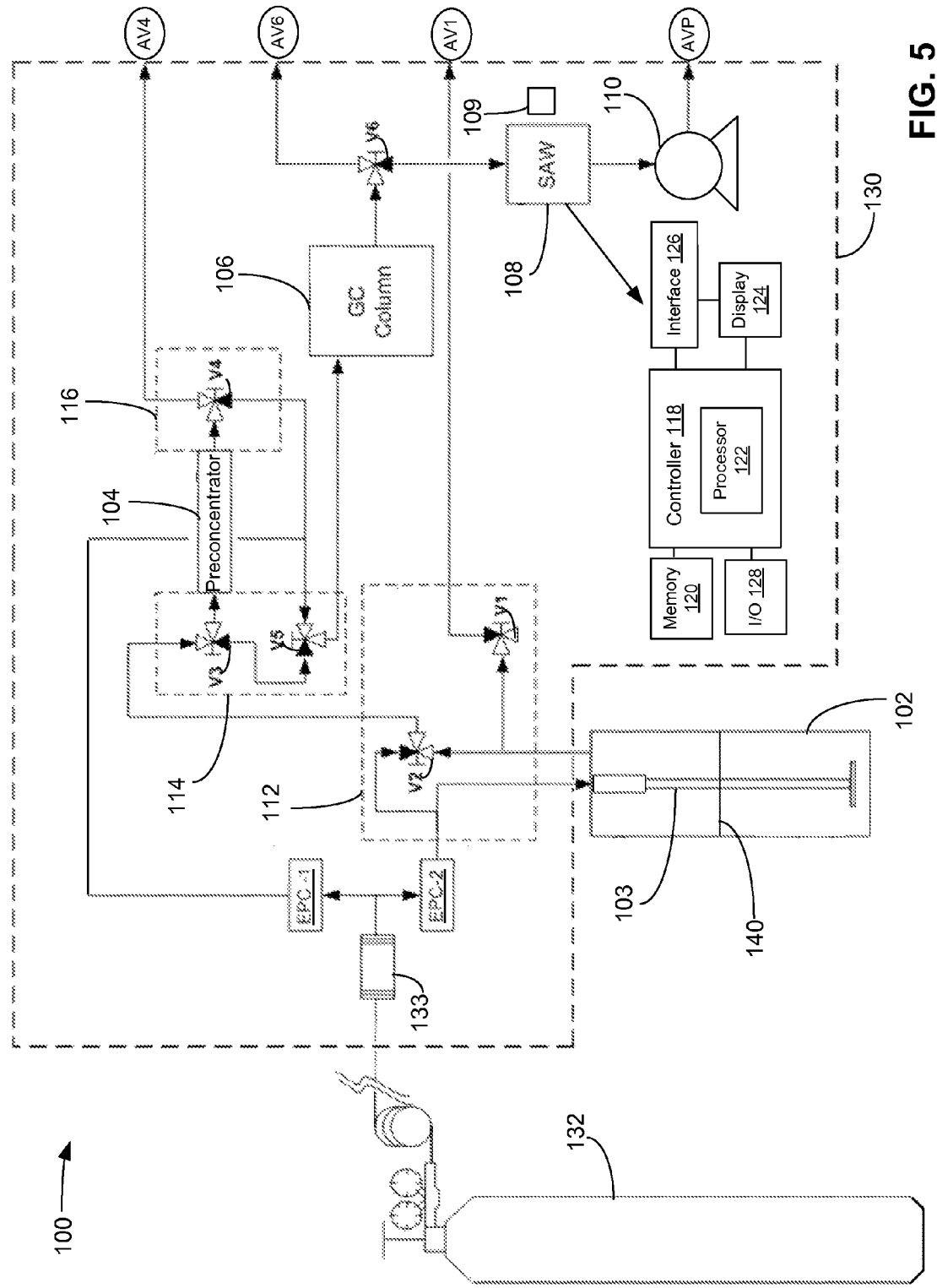
FIG. 5 is a schematic illustration of an exemplary chemical analysis system according to the invention in a purging state.

At step 1004, the system 100 is operated via the controller 118 to be in a purging state and the system 100 undergoes a purging process. The duration of the purging process may range from about 5 minutes to about 15 minutes. In one embodiment, the purging process is performed for about 10 minutes. FIG. 5 shows the system 100 in the purging state.

Electronic pressure controller EPC-2 and control valves V2, V3, and V4 are operated so that carrier gas passed through the sparger 103 and the sample vessel 102 flows through the preconcentrator 104 and is vented from the system 100 at exhaust port AV4. More specifically, a carrier gas from a supply 132 is passed through the sparger manifold 112 to the sparger 103. The carrier gas is introduced into the sample vessel 102 via the sparger 103 for passage through the water sample, and the carrier gas with entrained THM chemical compounds exits the sample vessel via the sparger manifold 112. The carrier gas with the entrained THM chemical compounds exits the sparger manifold 112 via control valve V2, enters the GC manifold 114, and passes to the preconcentrator 104 via control valve V3. The carrier gas having the entrained THM chemical compounds is passed through the preconcentrator 104 and the THM chemical compounds are adsorbed. The carrier gas exits the preconcentrator 104 at the preconcentrator manifold 116 and exits the system 100 through vent port AV4 via control valve V4. In one embodiment, the electronic pressure controller EPC-2 may regulate carrier gas flow to about 32 p.s.i. (220 kPa).

Electronic pressure controller EPC-1 and control valves V5 and V6 are operated so that carrier gas flows through the GC column 106 and is vented from the system 100 at exhaust port AV6. More specifically, carrier gas from the supply 132 is passed through the GC manifold 114 via control valve V5 to the GC column 106. The carrier gas exits the GC column 106 and exits the system 100 through exhaust port AV6 via control valve V6. In one embodiment, the electronic pressure controller EPC-1 may regulate carrier gas flow to about 10 p.s.i. (69 kPa).

The vacuum pump 110 may also be operated during the purging process and may apply a vacuum to the SAW detector 108 so that the pressure at the SAW coating of the SAW detector 108 is lowered (e.g. to about the vapor pressure of water). In some embodiments, this is performed at a constant temperature (e.g. the pressure at the coating is lowered without application of heat at the coating). For example, the temperature of the SAW coating may be about 30° C. Although in other embodiments, heat may be applied to the SAW coating (e.g. via a heating member 109) to increase the vapor pressure of the water. Moisture released from the SAW coating is vented from the system 100 via vent AVP. In the illustrated embodiment, no carrier gas flows through the SAW detector and no carrier gas flows across the SAW coating. In other embodiments, valve V6 may be controlled such that carrier gas flows across the SAW coating while the SAW detector 108 is under vacuum.

FIGS. 6-8 illustrate an exemplary sample vessel 102 and sparger 103 in accordance with the present invention. The arrangement of the sample vessel 102 and sparger 103 allows for easy grab sample analysis, while providing efficient sparging.

The sample vessel 102 is configured as a hollow body surrounding an internal volume 134 and defining a longitudinal axis, the sample vessel having an open top end 136 and a closed bottom end 138 (e.g. a graduated vessel). The sample vessel 102 may be made of any suitable material, such as glass, stainless steel or polymer. The sample vessel 102 is configured to hold a prescribed amount of water (or other suitable sample liquid) from which the chemicals of interest are to be purged. A fill line 140 (e.g. a laser etched or printed mark) is included along the longitudinal axis of the sample vessel 102 to denote a prescribed volume of water that is to be used in the analytical process. In one example, the fill line 140 denotes a prescribed volume of 40 mL. In other examples, the prescribed amount of water may be different, and the fill line 140 may denote a different prescribed amount (e.g. in the range of 20 to 50 mL).

The length, diameter, and thickness of the sample vessel 102 are configured such that there is sufficient distance between the bottom end 138 and the fill line 140, and such that there is sufficient distance between the fill line 140 and the top end 136. This ensures that there is sufficient purging of the THM chemical compounds from the liquid, and that there is sufficient travel distance from the water level in the sample vessel 102 to the top end 136 to allow water vapors to interact with each other and condense on the inner side wall of the sample vessel 102. This provides for a reduced amount of moisture passing through the preconcentrator 104 while sparging from the sample vessel 102. In an example wherein the fill line 140 denotes 40 mL of liquid, the level of liquid in the sample vessel 102 (e.g., the position of the fill line 40 relative to the bottom end 138) may be between 2.5 inches (6.35 cm) to 4 inches (10.16 cm), and the distance between the fill line 140 and the top end may 136 be between 3.5 inches (8.89 cm) to 5 inches (12.7 cm).

The sample vessel 102 is removably attached to the housing 130. The sample vessel 102 may include a retaining member, such as threads 142 or a protrusion (not shown) that is configured to retain the sample vessel 102 to the housing 130. The housing 130 may additionally include a complimentary retaining member 144. For example, the retaining member 144 may include a retaining tube nut, and the threaded sample vessel 102 may be attached thereto or removed therefrom (e.g. for grab sample analysis). Accordingly, the sample vessel 102 may be easily removed from the housing 130, filled with a water sample, and reattached to the housing 130.

The sample vessel 102 is coupled to the sparger manifold 112 (FIG. 1), which is an interface for the sample vessel 102 to provide a pathway for the delivery of carrier gas to the sample vessel 102, and to provide a pathway for the delivery of carrier gas including entrained THM chemical compounds to the preconcentrator 104.

The sparger 103 is connected to the sparger manifold 112 and is configured to pass carrier gas through the water sample. The design of the sparger 103 facilitates easy removal of the sample vessel 102 from the system 100, while optimizing adsorption of analyte (the THM chemical compounds) into the carrier gas.

The sparger 103 includes a tubular member 148 configured as an open-ended hollow body surrounding an internal volume 150 and defining a longitudinal axis, the tubular member 148 having a top end 152 and a bottom end 154. The tubular member 148 may be any suitable material, such as stainless steel, and may be any suitable size. For example, the outer diameter of the tubular member 148 may range from about 0.063 inches (0.16 cm) to about 0.125 inches (0.318 cm). The relatively small diameter of the tubular member 148 minimizes the immersed surface area available on which bubbles can coalesce, thereby minimizing the lost efficiency associated with this coalescing effect. The length of the tubular member 148 is substantially the length of the sample vessel 102, such that the bottom end 154 of the tubular member 148 is proximate the bottom end 138 of the sample vessel 102.

A gas dispersal member 156 is attached to the bottom end 154 of the tubular member 148, the gas dispersal member 156 having a diameter that closely corresponds to an internal diameter of the sample vessel 102. The gas dispersal member 156 includes a porous top 158 for distributing gas from the tubular member 148 across substantially the full width of the gas dispersal member 156.

More specifically, a porous member 160 is mounted to the bottom end 154 of the tubular member 148, the porous member 160 including a top major surface 162 and a bottom major surface 164 respectively facing in opposite longitudinal directions along longitudinal axis of the tubular member 148. In one example, the porous member 160 is a porous metal frit (e.g. a micron stainless steel frit) having a micron size ranging from 1 μm to 20 μm. A cap 166 is mounted to the porous member and forms with the porous member 160 a volume 168 extending over a major extent of the bottom major surface 164 and communicating with the internal volume 150 of the tubular member. The cap 166 encapsulates the bottom major surface 164 and side 170 of the porous member, leaving the top major surface 162 open to gas flow. The cap 166 may be any suitable material, such as stainless steel.

A check valve 171 may also be coupled to the top end 152 of the tubular member 148. The check valve 171 may be configured to restrict flow in the tubular member 148 from the bottom end 154 of the tubular member 148 to the top of the tubular member 152. The check valve 171 prevents moisture from entering the sparger manifold 112 via the tubular member 148.

The sparger 103 is designed to have a reduced volume so that when the water sample is present in the sample vessel 102, a sufficient distance from the water level in the sample vessel 102 to the top end 136 of the sample vessel 102 is maintained. This sparger 103 design also allows the flow of gas to enter the sample vessel 102 from the top end 136 (within the tubular member 148) and travel down the tubular member 148 to be released at the bottom end 138 of the sample vessel 102 and across substantially the entire diameter of the sample vessel 102. This arrangement optimizes the height and area of the gas bubble travel distance and contact time with the water to provide optimized gas dispersion through substantially the entire water sample, thereby optimizing adsorption of analyte (THM chemical compounds) into the carrier gas.

Figure 9:
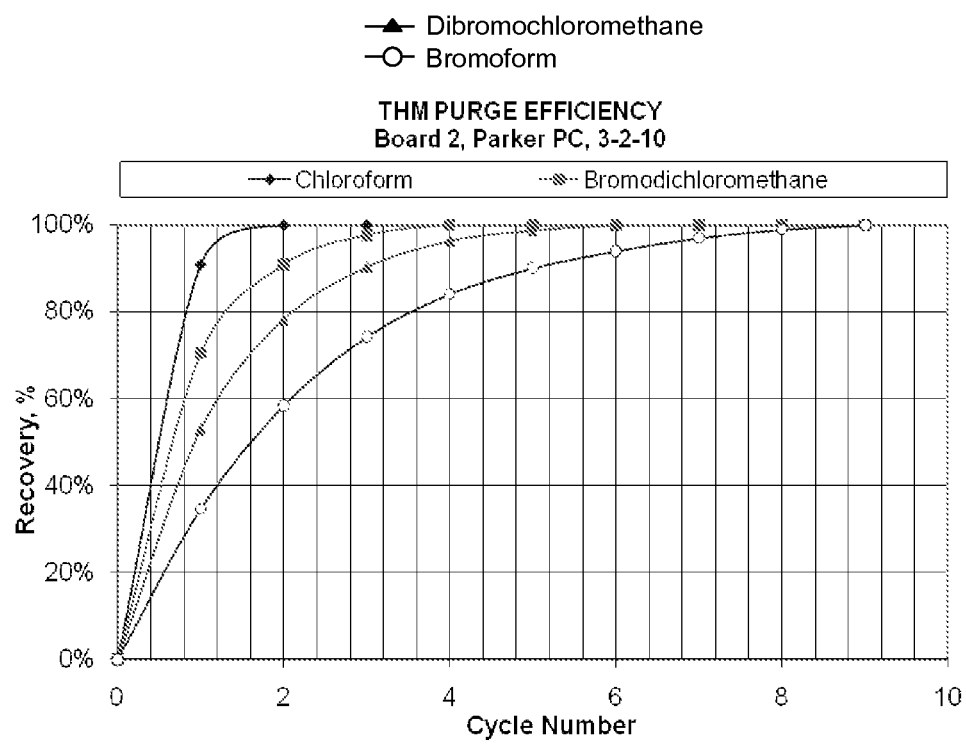
FIG. 9 is a graph showing the THM purge efficiency of the exemplary sparger used in the system with respect to various THM chemical compounds.

FIG. 9 shows the THM chemical compound purge efficiency of the exemplary sparger used in the system with respect to various trihalomethane chemicals, namely chloroform, bromodichloromethane, dibromochloromethane, and bromoform. To test the purge efficiency of the sparger 103, a known amount of each chemical compound was added to a water sample. The sample was placed in the sample vessel and subjected to multiple cycles of the analytical process 1000. FIG. 9 shows that approximately 100% of the chloroform added to the water sample was recovered after 2 cycles, approximately 100% of the bromodichloromethane added to the water sample was recovered after 4 cycles, approximately 100% of the dibromochloromethane added to the water sample was recovered after 2 cycles, and approximately 100% of the bromoform added to the water sample was recovered after 9 cycles.

The sparger 103 provides for improved efficiency over commercially available sparger tubes, which do not provide the action, contact time or energy required to quickly purge the compounds of interest from the water sample. Conventional spargers flow pressurized gas down into a vessel via a sintered metal element tube and emit gas along their length and diameter. Purge gas is permitted to flow out of the sparging tube along the length of the sintered metal. As water pressure increases within the depth of the sample the gas takes the path of least resistance generating more flow from the sparger tube in the top half of the sample column and less flow in the bottom half of the sample column. The gas flowing out of the upper portion of the element has minimum contact time with the water sample thus lowering the efficiency. In addition, the sparging action is limited to the center of the sample around the sparger tube providing minimal interaction with the sample around the circumference of the sparging vessel.

As described above, the carrier gas with the entrained THM chemical compounds exits the sparger manifold 112 via control valve V2, enters the GC manifold 114, and is passed through the preconcentrator 104. Conventional purge and trap systems typically heat the gaseous sample path between the water sample and the preconcentrator to maintain the VOCs to be in the vapor phase. However, in embodiments of the exemplary system 100 according to the present invention, the path from the sample vessel 102 to the preconcentrator 104 may not be heated. The manifolds 112, 114 reduce the travel distance of the carrier gas and therefore reduce the likelihood of the THM chemical compounds condensing in the path, even without any heating.

The carrier gas having the entrained THM chemical compounds is passed through the preconcentrator 104 during the purging process 1004. FIGS. 11-12 illustrate exemplary preconcentrators 104 in accordance with the present invention. The preconcentrator 104 is configured to adsorb the THM chemical compounds while the carrier gas having the entrained THM chemical compounds is passed therethrough. A preferred preconcentrator 104 is one that is designed to have 1) high efficiency chemical scrubbing, 2) sufficient chemical capacity for downstream analytical analysis, 3) minimal size, 4) minimal thermal mass for low power thermal desorption of the entrapped chemicals, and/or 5) a built-in heater.

The preconcentrator 104 may be, for example, one or more metal tubular members 172 of small diameter, e.g. less than about 0.20 inch (0.51 cm) outer diameter, disposed between the GC manifold 114 and the PC manifold 116. In one example, the tubular member 172 may have a length of about 2 inches (5.1 cm) and an outer diameter of about 0.125 inches (0.32 cm). The tubular member 172 may be coated on its inner and outer diameter surfaces with a passivating material such as trimethyl siloxane.

With reference to FIGS. 11 and 12, a sorbent bed 178 is disposed in the tubular member 172 and may include a suitable adsorbing material such as fine mesh, commercial chemical adsorbent beads. For example, a sorbent bed 178 (e.g. approximately 1 inch in length) may include Tenax™ TA porous polymer resin material available from Buchem B.V.

First and second porous retaining members 180, 182 are disposed in the tubular member 172 at opposite ends of the sorbent bed 178 for retaining the sorbent bed 178. The first and second porous retaining members 180, 182 are constrained against movement by respective inwardly crimped portions 184, 186 of the tubular member 172. The inwardly crimped portions 184, 186 allow consistent placement of the porous retaining members 180, 182 (e.g. porous metal frits) and uniform sorbent bed packing. For example, after the preconcentrator 104 including the first retaining member 180 is filled with the specified mass of adsorbent, the second retaining member 182 is added and the tubular member 172 crimped to prevent movement under pressure.

FIG. 11 shows an embodiment of the preconcentrator 104 wherein the first and second retaining members 180, 182 are immediately adjacent the sorbent bed 178. In other embodiments (e.g. shown in FIG. 12), an additional component 188, such as a spacer, ceramic wool or glass wool is additionally disposed in the preconcentrator 104 (e.g., between the sorbent bed 178 and the second retaining members 180, 182). The arrangement of ceramic wool and/or glass wool between the sorbent bed 104 and the retaining member 180, 182 may prevent small particles of adsorbent from being deposited onto the GC column 106, and also may act as a focusing material for organic compounds of different volatility. The focusing effect ensures that a concentrated, small volume of carrier gas is deposited onto the GC column 106.

FIG. 10 shows a preconcentrator (PC) housing assembly 169 disposed between the GC manifold 114 and the PC manifold 116. The PC housing assembly 169 includes a tubular member 173 that defines an interior volume in which the preconcentrator 104 is removably disposed. As further illustrated in FIG. 10A, which shows a partial cross-sectional view of parts of the PC housing assembly 169 and the preconcentrator 104, taken along line 10-10 of FIG. 10, the outer diameter of the tubular member 172 of the preconcentrator 104 may be substantially the same as the interior diameter of the tubular member 173. In one example, the tubular member 173 may have an interior diameter of about 0.125 inches (0.32 cm). FIG. 10A does not show the sorbent bed 178, the porous retaining members 180, 182, and/or the additional component 188 disposed in the tubular member 172.

The tubular member 173 may be wrapped with a resistance heater 174 that is coupled to heater wires 176. The PC housing assembly may be attached at respective ends to the GC manifold 114 and the PC manifold 116 via retaining members 175 (e.g. threads, nuts, etc.).

As described above, the preconcentrator 104 may be removed from the housing and system via access port 131. More specifically, the access port 131 provides access to the GC manifold 114 or the PC manifold 116, and the preconcentrator 104 disposed in the tubular member 173 of the PC housing assembly 169 may be passed the GC manifold 114 or the PC manifold 116. A preconcentrator 104 having spent adsorbent may be removed from the system 100 and repacked with new adsorbent or replaced with a new preconcentrator.

Figure 13:
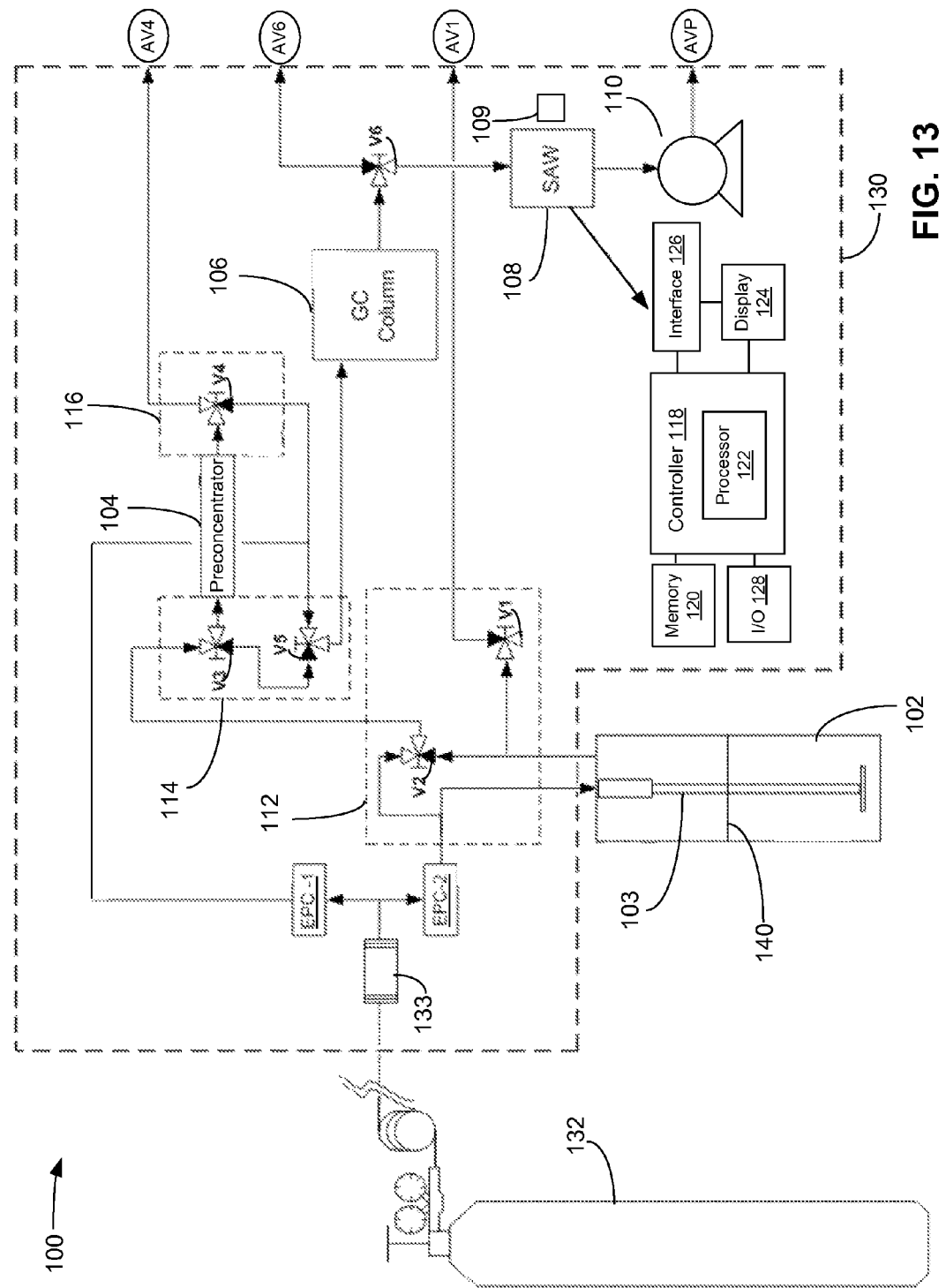
FIG. 13 is a schematic illustration of an exemplary chemical analysis system according to the invention in a water removal state.

At step 1006, the system 100 is operated via the controller 118 to be in a water removal state and the system 100 undergoes a water removal process (e.g. a dry purge process). The water removal process exhausts moisture from the preconcentrator 104 prior to desorption of the THM chemical compounds. The duration of the water removal process may range from about 0 seconds to about 3 minutes. In one embodiment, the water removal process is performed for about 1 minute. FIG. 13 shows the system 100 in the water removal state. Electronic pressure controller EPC-2 and control valves V2, V3, and V4 are operated by the controller 118 so that carrier gas bypasses the sparger 103 and sample vessel 102, flows through the preconcentrator 104, and is vented from the system 100 at exhaust port AV4. More specifically, the carrier gas from the supply 132 is passed through the sparger manifold 112 to the GC manifold 114 (via control valves V2 and V3), through the preconcentrator 104 and preconcentrator manifold 116 (via control valve V4), and exits the system through vent port AV4. The electronic pressure controller EPC-2 may regulate carrier gas flow to about 32 p.s.i. (220 kPa).

Electronic pressure controller EPC-1 and control valves V5 and V6 are operated so that carrier gas flows through the GC column and the SAW detector. More specifically, carrier gas from the supply 132 is passed through the GC manifold 114 via control valve V5 to the GC column 106. The carrier gas exits the GC column 106 and is passed through the SAW detector 110 via control valve V6. The electronic pressure controller EPC-1 may regulate carrier gas flow to about 10 p.s.i. (69 kPa).

The vacuum pump 110 may also be operated during the water removal process and may apply a vacuum to the SAW coating so that the pressure at the SAW coating of the SAW detector 110 is lowered (e.g. to about the vapor pressure of water). In some embodiments, this is performed at a constant temperature (e.g. the pressure at the coating is lowered without application of heat at the coating). For example, the temperature of the SAW coating may be about 30° C. Although in other embodiments, heat may be applied to the SAW coating (e.g. via a heating member 109) to increase the vapor pressure of the water. Moisture released from the SAW coating and the carrier gas passed through the SAW detector is vented from the system 100 via vent AVP. In the illustrated embodiment, valve V6 is controlled such that carrier gas flows across the SAW detector while the SAW is under vacuum. In other embodiments, no carrier gas flows across the SAW coating.

Figure 14:
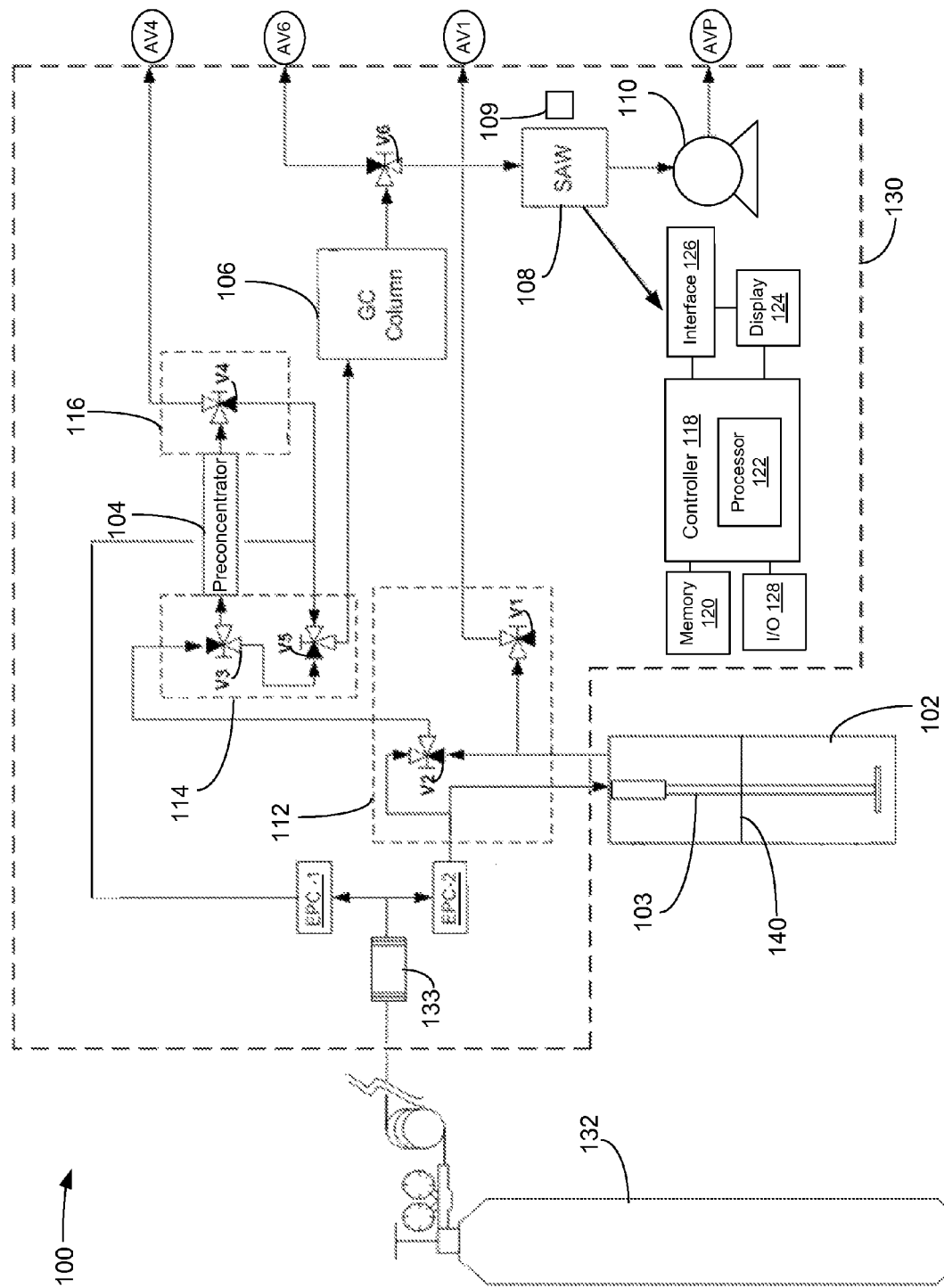
FIG. 14 is a schematic illustration of an exemplary chemical analysis system according to the invention in a second ventilation state.

At step 1008, the system 100 is operated via the controller 118 to be in a second ventilation state and the system 100 undergoes a second ventilation process. The duration of the second ventilation process may range from about 0 seconds to about 10 seconds. In one embodiment, the second ventilation process is performed for about 5 seconds. FIG. 14 shows the system 100 in the second ventilation state. The electronic pressure controllers EPC-2 is controlled via controller 118 such that no flow of carrier gas is passed therethrough. Control valve V1 is operated to provide a flow path from the sparger 103 and sample vessel 102 to vent AV1. Additionally, Electronic pressure controller EPC-1 and control valves V5 and V6 are operated so that carrier gas flows through the GC column and the SAW detector. The electronic pressure controller EPC-1 may regulate carrier gas flow to about 10 p.s.i. (69 kPa).

The vacuum pump 110 may also be operated during the second ventilation step and may apply a vacuum to the SAW coating so that the pressure at the SAW coating of the SAW detector 110 is lowered (e.g. to about the vapor pressure of water). In some embodiments, this is performed at a constant temperature (e.g. the pressure at the coating is lowered without application of heat at the coating). For example, the temperature of the SAW coating may be about 30° C. Although in other embodiments, heat may be applied to the SAW coating (e.g. via a heating member 109) to increase the vapor pressure of the water. Moisture released from the SAW coating and the carrier gas passed through the SAW detector is vented from the system 100 via vent AVP.

At step 1010, the system 100 is operated via the controller 118 to be in a desorption state and the system 100 undergoes a desorption process. The preconcentrator 104 is heated to desorb the purged THM chemical compounds for passage (via the carrier gas) through the GC column 106. In one embodiment, the preconcentrator 104 is heated to about 240° C. (via resistance heater 174 of PC housing assembly 169). The duration of the desorption process may range from about 0 seconds to about 3 minutes. In one embodiment, the desorption process is performed for about 90 seconds.

Figure 15:
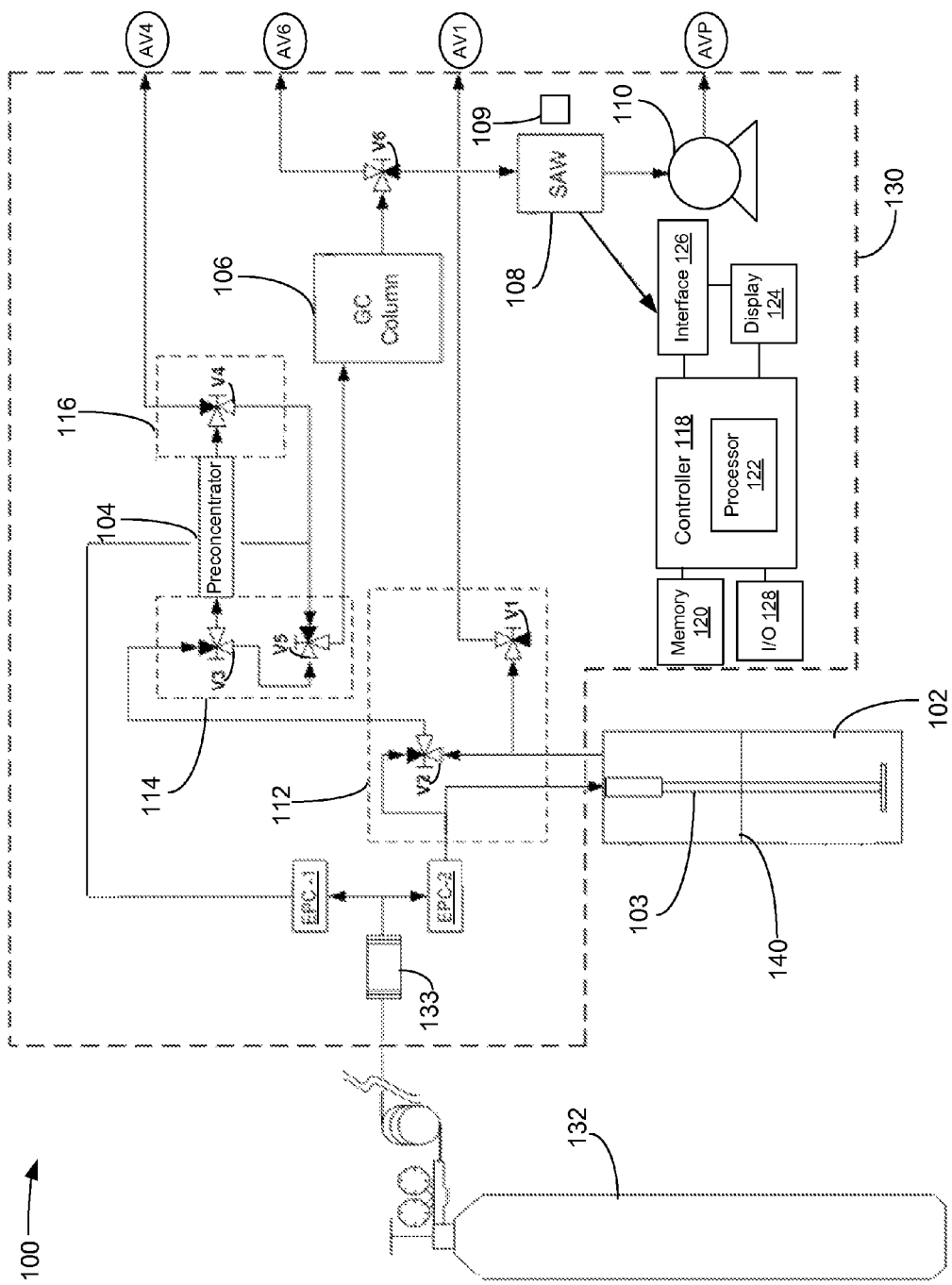
FIG. 15 is a schematic illustration of an exemplary chemical analysis system according to the invention in a desorption state.

FIG. 15 shows the system 100 in the desorption state. The electronic pressure controller EPC-2 is controlled via controller 118 such that no flow of carrier gas is passed therethrough. Electronic pressure controller EPC-1 and control valves V4, V3, V5, and V6 are operated so that carrier gas flows through the preconcentrator 104 and the GC column 106 and is vented from the system 100 at vent AV6. More specifically, a carrier gas from the supply 132 is passed through the PC manifold 116 to the preconcentrator 104. The carrier gas is passed through the preconcentrator 104, exits the preconcentrator 104 at the GC manifold 114, and passes through the GC manifold 114 via control valves V3 and V5. Flow through the preconcentrator 104 in the desorption process is countercurrent to the flow through the preconcentrator during the purging process. The carrier gas exiting the GC manifold passes through the GC column 106 and is vented from the system 100 via control valve V6. In one embodiment, the electronic pressure controller EPC-1 may regulate carrier gas flow to about 10 p.s.i. (69 kPa).

At step 1012, the system 100 is operated via the controller to be in a pre-GC state and the system 100 undergoes a pre-GC process. The duration of the pre-GC process may range from about 0 seconds to about 3 minutes. In one embodiment, the pre-GC process may be performed for about 100 seconds. During the pre-GC process, carrier gas passed through the GC column 106 following the desorption process is vented from the system 100. This carrier gas is typically a moisture-laden effluent stream from the GC column 106, and venting this carrier gas from the system will minimize moisture exposure at the SAW coating. During this process, the temperature of the GC column 104 ranges from about 27° C. to about 37° C. (e.g. ambient temperature). In one embodiment, the temperature of the GC column is about 30° C. The temperature of the preconcentrator 104 may be about 150° C. (e.g. the preconcentrator 104 may be cooled from the previous desorption process via a cooling member such as a fan (not illustrated)).

Figure 16:
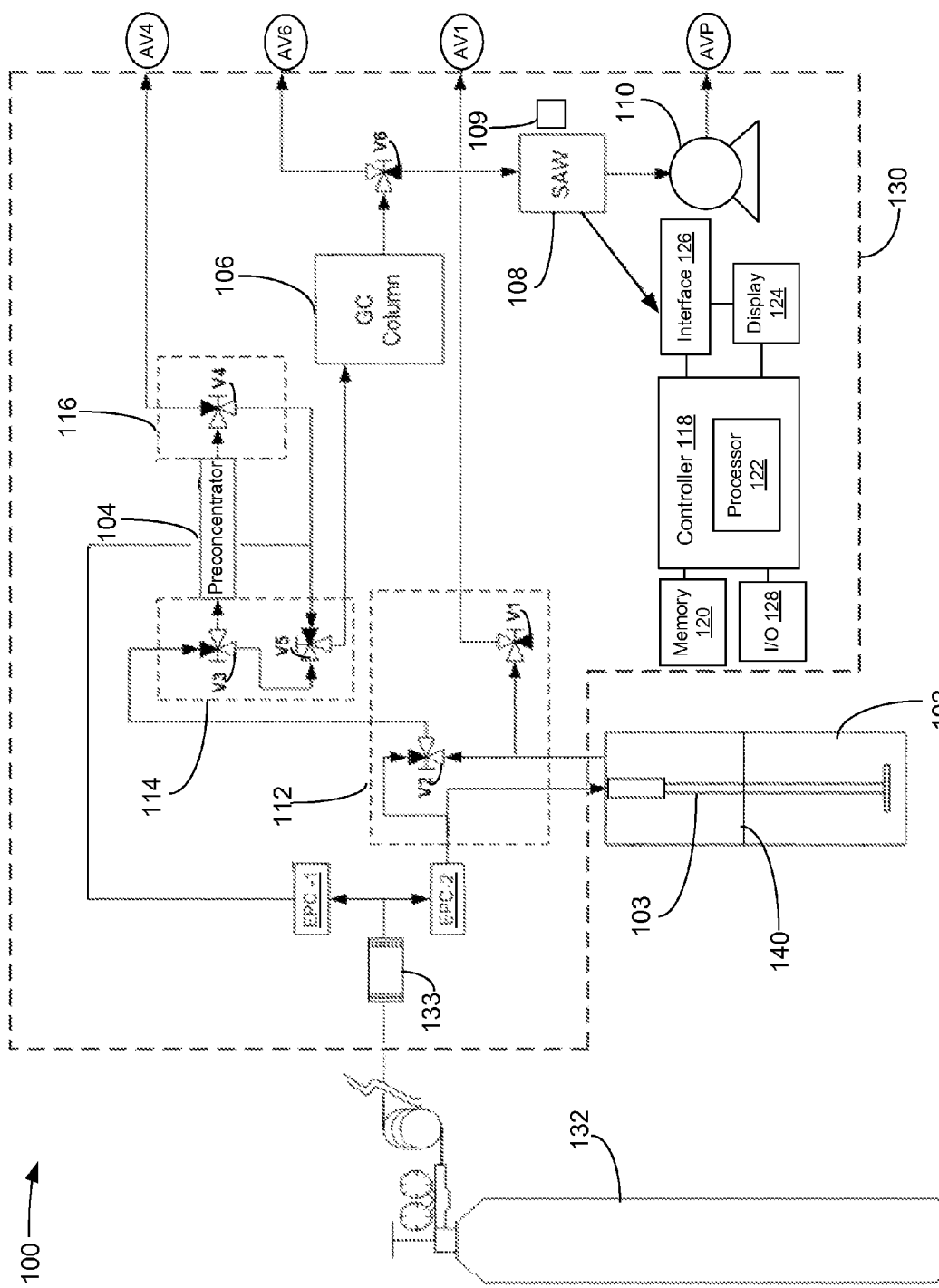
FIG. 16 is a schematic illustration of an exemplary chemical analysis system according to the invention in a pre-GC state.

FIG. 16 shows the system 100 in the pre-GC state. The electronic pressure controller EPC-2 is controlled via controller 118 such that no flow of carrier gas is passed therethrough. Electronic pressure controller EPC-1 and control valves V4, V3, V5, and V6 are operated so that carrier gas flows through the preconcentrator 104 and the GC column 106 and is vented from the system 100 at vent AV6. More specifically, a carrier gas from the supply 132 is passed through the PC manifold 116 to the preconcentrator 104. The carrier gas is passed through the preconcentrator 104, exits the preconcentrator 104 at the GC manifold 114, and passes through the GC manifold 114 via control valves V3 and V5. Flow through the preconcentrator 104 in the pre-GC process is countercurrent to the flow through the preconcentrator during the purging process. The carrier gas exiting the GC manifold passes through the GC column 106 and is vented from the system 100 via control valve V6. In one embodiment, the electronic pressure controller EPC-1 may regulate carrier gas flow to about 10 p.s.i. (69 kPa).

Figure 17:
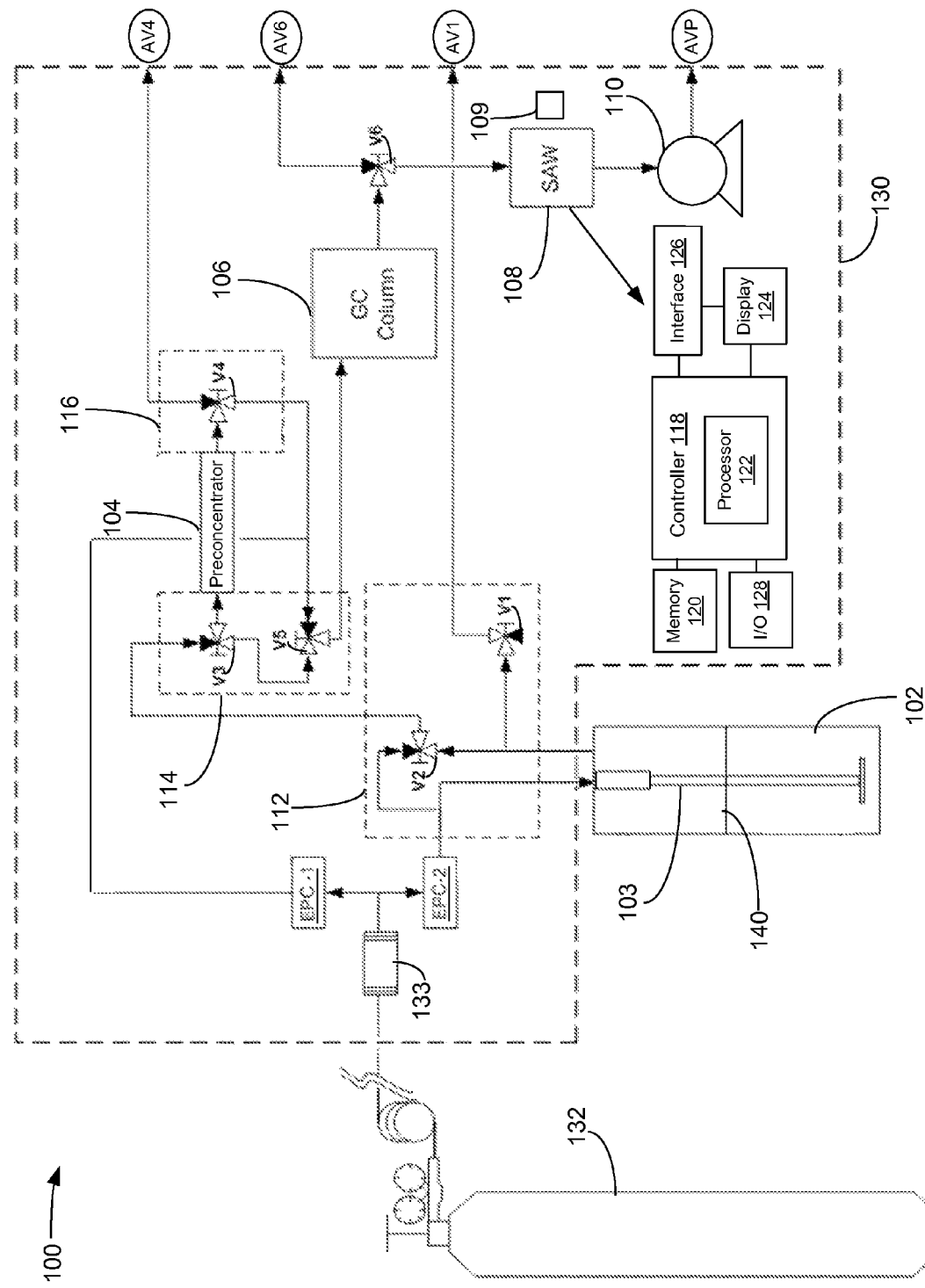
FIG. 17 is a schematic illustration of an exemplary chemical analysis system according to the invention in a GC state.

At steps 1014 and 1016, the system 100 is operated via the controller to be in a GC state and the system 100 undergoes first and second GC processes. FIG. 17 shows the system 100 in the GC state. The electronic pressure controller EPC-2 is controlled via controller 118 such that no flow of carrier gas is passed therethrough. Electronic pressure controller EPC-1 and control valves V4, V3, V5, and V6 are operated so that carrier gas flows through to the preconcentrator 104, then through the GC column 106, and finally to the SAW detector 108. More specifically, a carrier gas from the supply 132 is passed through the PC manifold 116 to the preconcentrator 104. The carrier gas is passed through the preconcentrator 104, exits the preconcentrator 104 at the GC manifold 114, and passes through the GC manifold 114 via control valves V3 and V5. Flow through the preconcentrator 104 is countercurrent to the flow through the preconcentrator during the purging process. The carrier gas exiting the GC manifold passes through the GC column 106 to the SAW detector 108 via control valve V6.

During the GC processes, the GC column 106 and the preconcentrator 104 may be operated at an elevated temperature and pressure. The duration of the GC processes may collectively range from about 5 minutes to about 10 minutes. In one embodiment, the first GC process 1014 is performed for about 225 seconds, the temperature of the preconcentrator 104 is about 150° C., the temperature of the GC column is about 100° C., and the electronic pressure controller EPC-1 regulates carrier gas flow to about 22 p.s.i. (152 kPa). In one embodiment, the second GC process 1014 is performed for about 180 seconds, the temperature of the preconcentrator 104 is about 150° C., the temperature of the GC column is about 200° C., and the electronic pressure controller EPC-1 regulates carrier gas flow to about 30 p.s.i. (207 kPa).

The carrier gas is therefore passed through the preconcentrator 104 at a relatively high pressure. In some embodiments, the carrier gas may be passed through the preconcentrator 104 between about 10 p.s.i. (69 kPa) and about 60 p.s.i. (414 kPa). A stabilized adsorbent bed 178 is preferred for this high pressure application to prevent band broadening, retention time fluctuation and negative sensitivity effects due to adsorbent bed displacement. The design of the preconcentrator 104 (e.g. as described above with reference to FIGS. 10-12) is suitable for such application. The use of higher pressure carrier gas flow along with high temperature allows the transmission of the desorbed THM chemical compounds onto the GC column 106 without use of a conventional inject valve operation. The elimination of a multiport or GC inject valve reduces operational complexity and minimizes gas volume (which helps to improve sensitivity).

Figure 18:
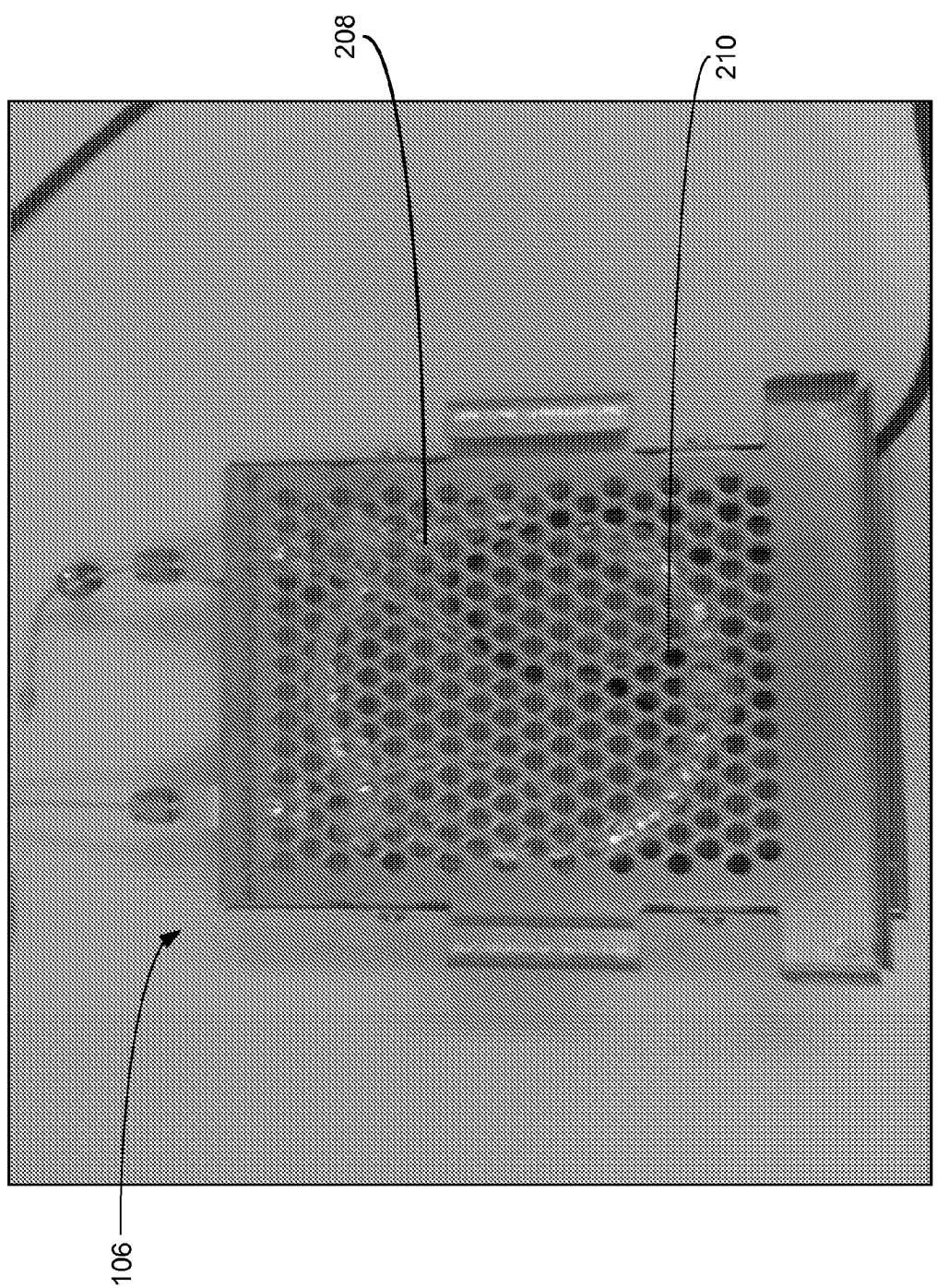
FIG. 18 is a depiction of an exemplary GC column used in the system.

FIG. 18 depicts an exemplary GC column 106 in accordance with the present invention. The GC column 106 partially retains the THM chemical compounds with different affinities as they pass through the column resulting in different retention times for each compound, thereby spreading out the time each compound is delivered to the detector, so that temporal overlap does not occur or is minimized. The GC column 106 may be a capillary tube 208 that is, for example, compactly coiled and has a length, for example, of 30 meters. In other embodiments, the GC column 106 may be a larger bore column, such as a wide bore column or a mega bore column. The tube has associated therewith a suitable heater 210 for heating the tube to a prescribed temperature, as at a constant or controlled ramping temperature, for sequential desorption of the compounds for sequential passage to the SAW detector 108.

The SAW detector 108 includes a piezoelectric element having a surface coated on its sensing surface with a material selected to adsorb and interact with the VOCs to be detected. Interaction of the chemical with the material coating of the sensing element alters one or more properties of a surface acoustic wave, and the electrodes on the piezoelectric element detect the altered wave, producing an electrical signal.

In one embodiment, the SAW detector 108 is a 100 MHz device coated with nanoporous carbon by use of pulsed laser deposition. In some embodiments, the operating frequency of the SAW ranges from about 10 MHz to about 200 MHz. In other embodiments, the operating frequency of the SAW ranges from about 50 MHz to about 200 MHz. The nanoporous carbon coating is not susceptible to degradation when subjected to chloroform and other VOCs, as were previously used polymer coatings. This provides a longer life of the coating. Although, in some embodiments, a polymer coating may be used.

Figure 19:
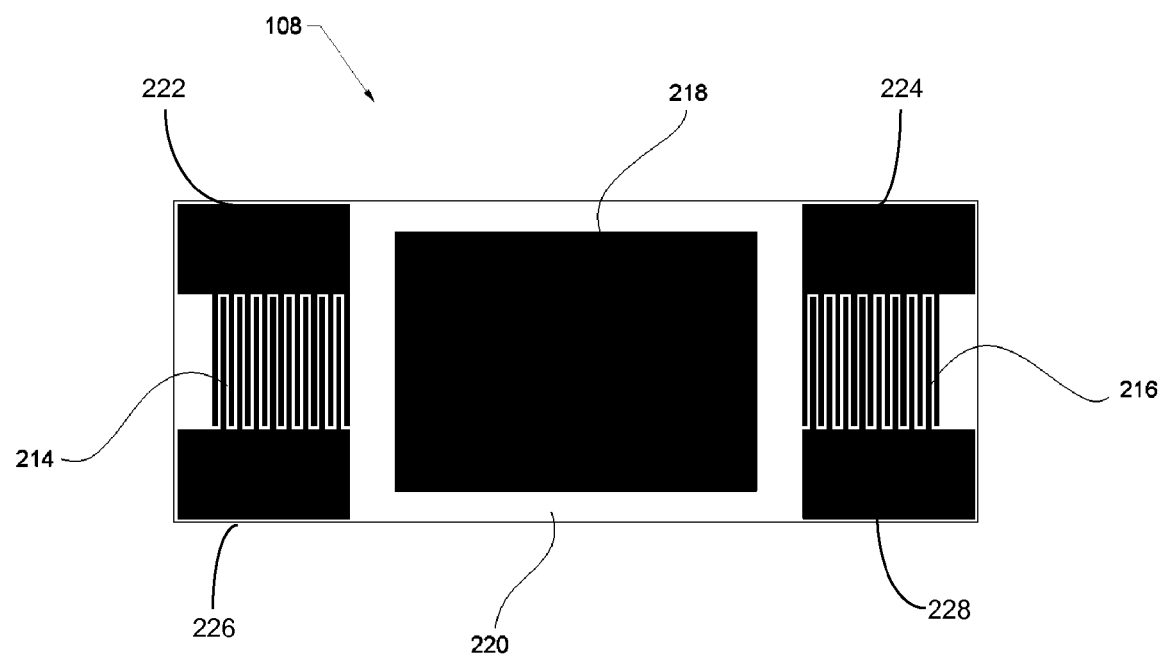
FIG. 19 is a depiction of an exemplary SAW detector including a nanoporous carbon coating.
Figure 20:
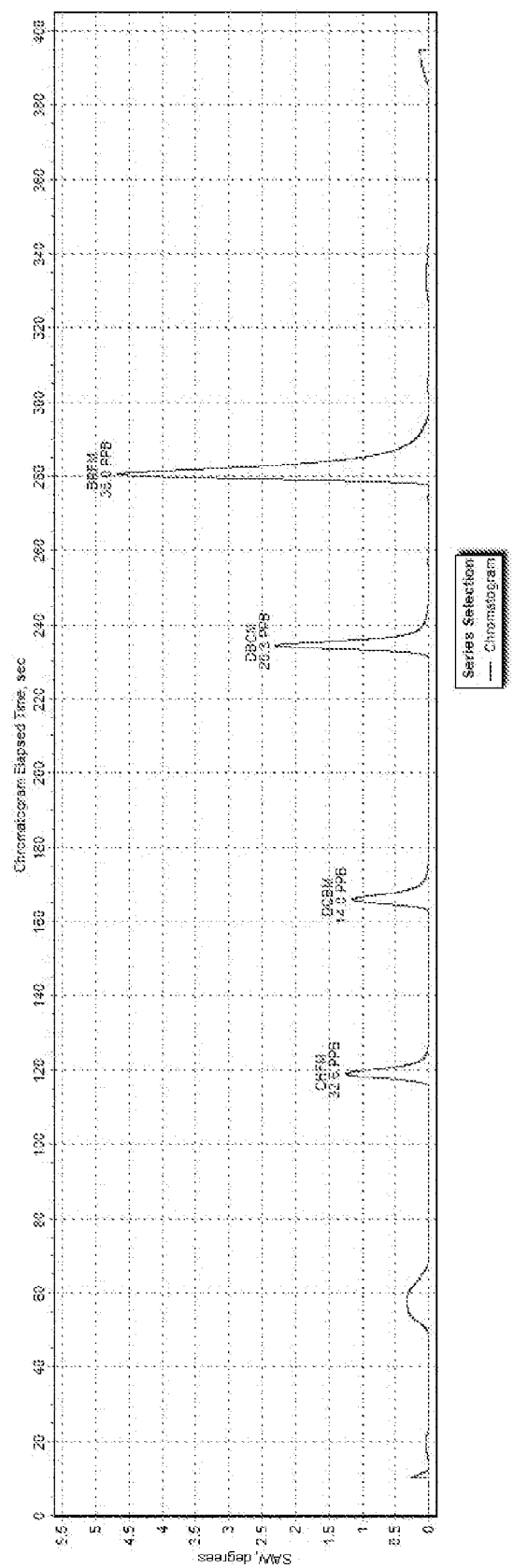
FIG. 20 is a graph showing exemplary results obtained from a water sample including four THM chemical compounds using the system according to the invention.

FIG. 19 is a depiction of an exemplary 100 MHz SAW detector 108 including input and output transducers (e.g. IDT fingers) 214 and 216 and having a nanoporous carbon coating 218 applied to the sensing surface 220 of the SAW detector 108 using pulsed-laser deposition. The SAW detector 108 also includes Pogo pin contact points 222, 224, 226, and 228. The nanoporous carbon coating 218 adsorbs and desorbs the organic compounds. The frequency of the SAW device changes as a function of the change in adsorbed mass of these organic compounds. This change of frequency is converted into a voltage signal according to mass adsorption and desorption on the SAW device. Data from the signal may be collected, analyzed, and displayed at the display 124 (e.g. via the controller 118). For example, FIG. 20 shows the results obtained from a water sample containing four different concentrations of trihalomethanes, namely chloroform, dichlorobromomethane (DCBM), dibromochloromethane (DBCM), and bromoform.

Figure 21:
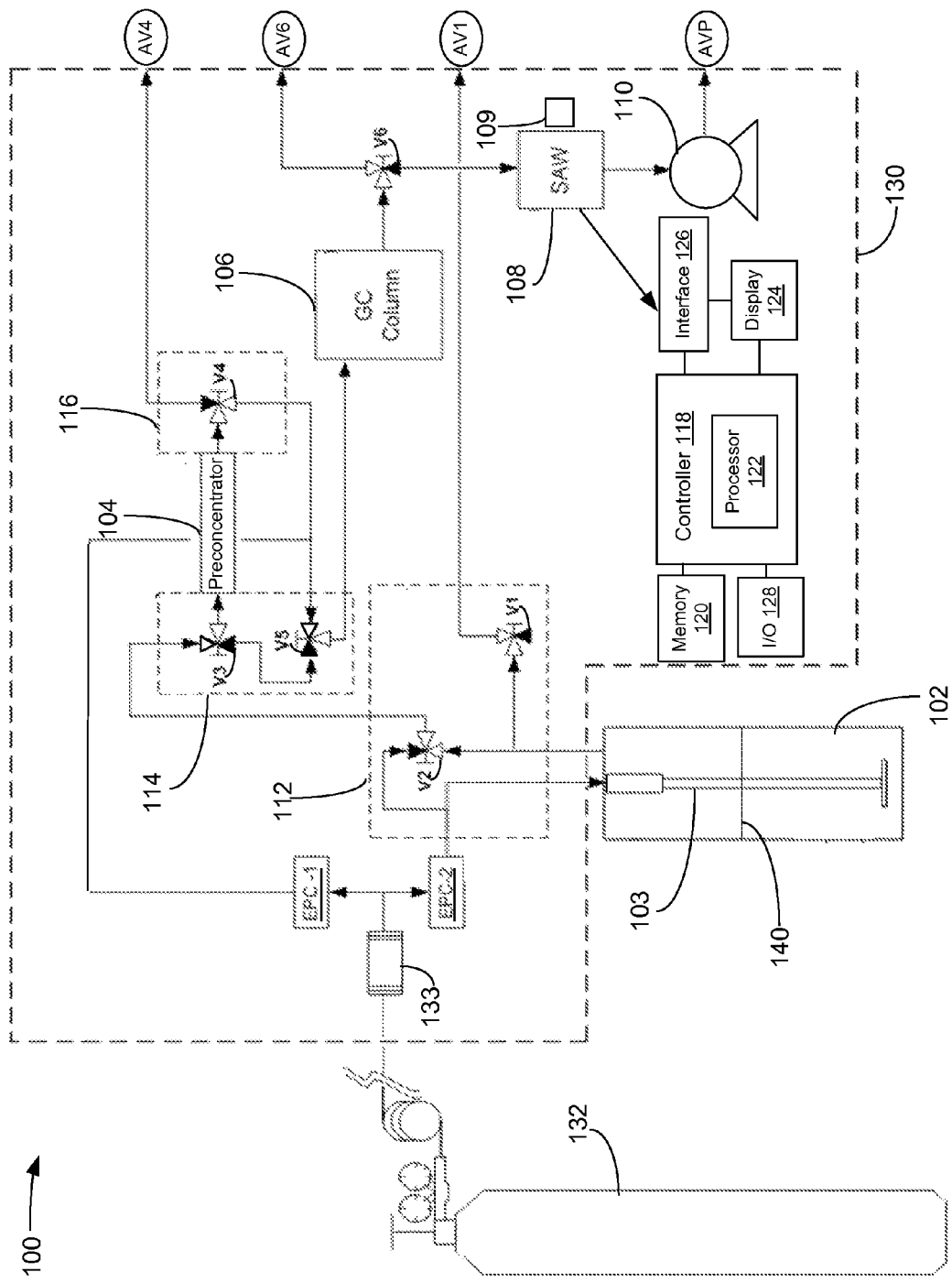
FIG. 21 is a schematic illustration of an exemplary chemical analysis system according to the invention in a cool down state.

At step 1018, the system 100 is operated via the controller 118 to be in a cool down state and the system 100 undergoes a cool down process. The duration of the cool down process may range from about 0 seconds to about 3 minutes. In one embodiment, the cool down process is performed for about 100 seconds and the temperature of the GC column 106 is lowered to about 75° C. (e.g. the GC column 106 may be cooled from the previous desorption process via a cooling member such as a fan (not illustrated)). FIG. 21 shows the system 100 in the cool down state. The electronic pressure controller EPC-2 is controlled via controller 118 such that no flow of carrier gas is passed therethrough. Electronic pressure controller EPC-1 and control valves V4, V3, V2, V1, V5, and V6 are operated so that a portion of the carrier gas flows through the preconcentrator 104 and is vented from the system at vent AV1, and so that another portion of the carrier gas flows through the GC column 106 and is vented from the system 100 at vent AV6. More specifically, a portion of the carrier gas from the supply 132 is passed through the PC manifold 116 to the preconcentrator 104. The carrier gas is passed through the preconcentrator 104, exits the preconcentrator 104 at the GC manifold 114, and passes through the GC manifold 114 via control valve V3. Flow through the preconcentrator 104 is countercurrent to the flow through the preconcentrator during the purging process. The carrier gas exiting the GC manifold 114 via control valve V3 passes through the sparger manifold 112 via control valves V2 and V1, and is vented from the system 100 via control valve AV1. Another portion of the carrier gas from supply 132 is passed through the GC manifold 114 via control valve V5. The carrier gas exiting the GC manifold via control valve V5 passes through the GC column 106 and is vented from the system 100 via control valve V6. In one embodiment, the electronic pressure controller EPC-1 may regulate carrier gas flow to about 8 p.s.i. (55 kPa).

At step 1020, the system is operated via the controller 118 to be in a SAW vacuum state and the system 100 undergoes a SAW vacuum process. The release of moisture via the vacuum process happens quickly and there is little improvement in SAW sensitivity gained by extending the time at vacuum beyond a few minutes. The duration of the SAW vacuum process may range from about 0 seconds to about 3 minutes. In one embodiment, the SAW vacuum process is performed for about 150 seconds.

Figure 22:
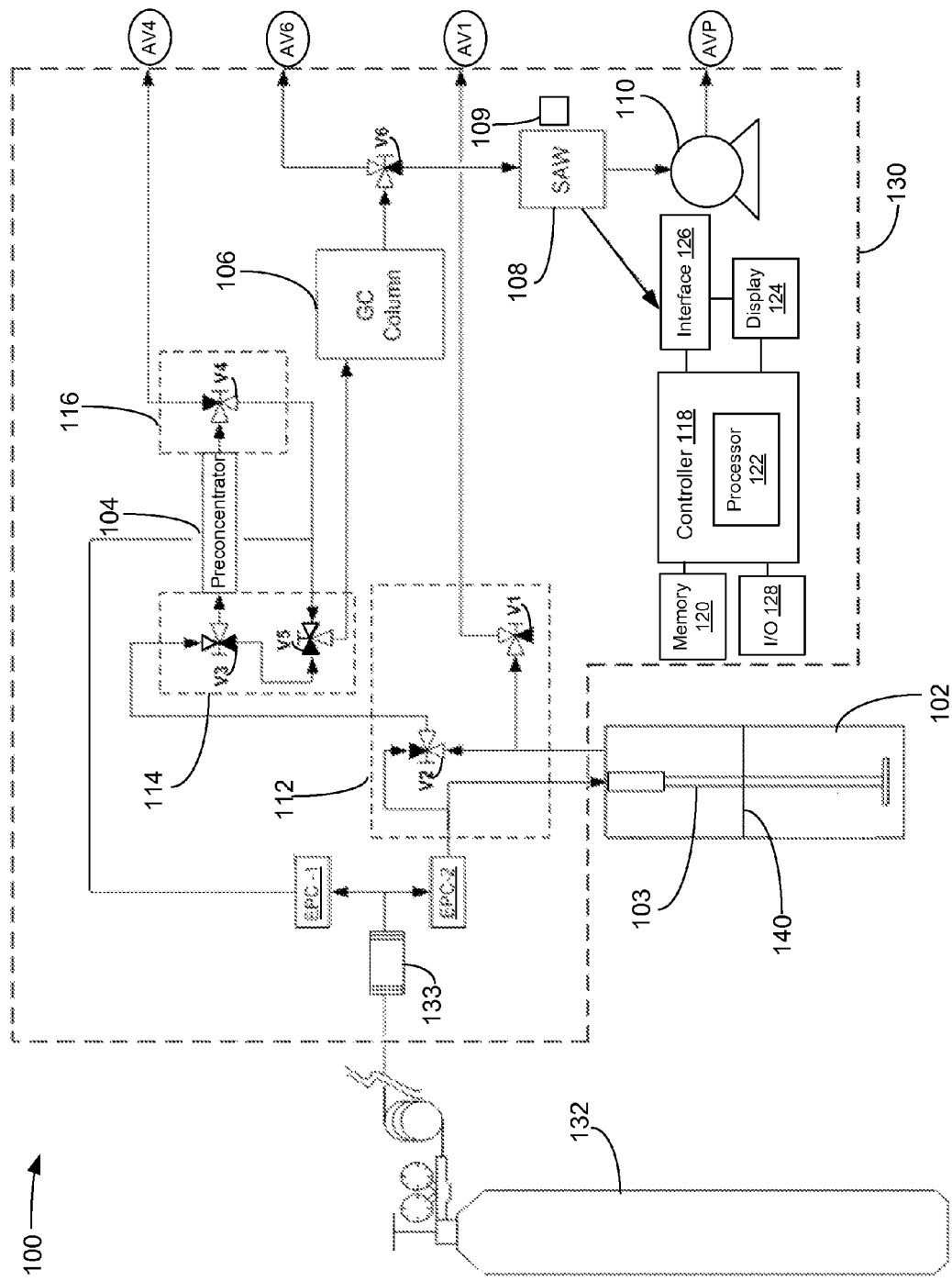
FIG. 22 is a schematic illustration of an exemplary chemical analysis system according to the invention in a SAW vacuum state.

FIG. 22 shows the system 100 in the SAW vacuum state. The electronic pressure controller EPC-2 is controlled via controller 118 such that no flow of carrier gas is passed therethrough. Electronic pressure controller EPC-1 and control valves V4, V3, V2, V1, V5, and V6 are operated so that a portion of the carrier gas flows through the preconcentrator 104 and is vented from the system at vent AV1, and another portion of the carrier gas flows through the GC column 106 and is vented from the system 100 at vent AV6. More specifically, a portion of the carrier gas from the supply 132 is passed through the PC manifold 116 to the preconcentrator 104. The carrier gas is passed through the preconcentrator 104, exits the preconcentrator 104 at the GC manifold 114, and passes through the GC manifold 114 via control valve V3. Flow through the preconcentrator 104 during the SAW vacuum process is countercurrent to the flow through the preconcentrator during the purging process. The carrier gas exiting the GC manifold 114 via control valve V3 passes through the sparger manifold 112 via control valves V2 and V1, and is vented from the system 100 via control valve AV1. Another portion of the carrier gas from supply 132 is passed through the GC manifold 114 via control valve V5. The carrier gas exiting the GC manifold via control valve V5 passes through the GC column 106 and is vented from the system 100 via control valve V6. In one embodiment, the electronic pressure controller EPC-1 may regulate carrier gas flow to about 8 p.s.i. (55 kPa).

The vacuum pump 110 is controlled so that the pressure at the SAW coating of the SAW detector 110 is lowered (e.g. to about the vapor pressure of water). In some embodiments, this is performed at a constant temperature (e.g. the pressure at the coating is lowered without application of heat at the coating). For example, the temperature of the SAW coating may be about 30° C. Although in other embodiments, heat may be applied to the SAW coating (e.g. via a heating member (not shown)) to increase the vapor pressure of the water. The lowered pressure aids in the release (evaporation) of moisture embedded in the SAW coating that otherwise would not be released simply by passing carrier gas across the SAW coating. Moisture released from the SAW coating is vented from the system 100 via vent AVP. In the illustrated embodiment, no carrier gas flows across the SAW coating. In other embodiments, valve V6 may be controlled such that carrier gas flows across the SAW detector while the SAW is under vacuum.

Figure 23:
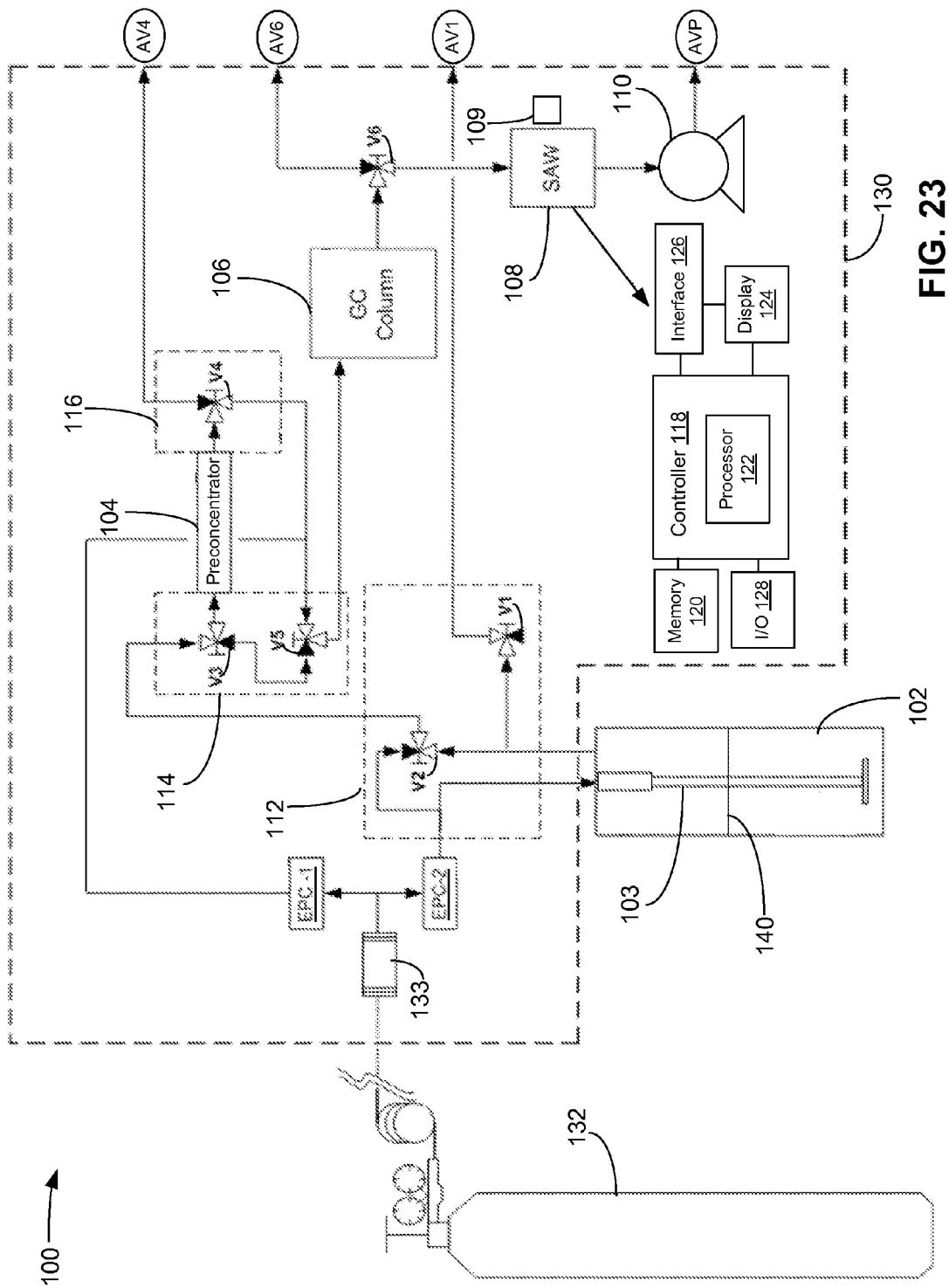
FIG. 23 is a schematic illustration of an exemplary chemical analysis system according to the invention in a SAW fill state.

At step 1022, the system is operated via the controller 118 to be in a SAW fill state and the system 100 undergoes a SAW fill process in which the carrier gas is passed through the SAW detector 108 without the application of vacuum from the vacuum pump 110. The duration of the SAW fill process may range from about 0 seconds to about 3 minutes. In one embodiment, the SAW fill process is performed for about 90 seconds. FIG. 23 shows the system 100 in the SAW fill state. The electronic pressure controller EPC-2 is controlled via controller 118 such that no flow of carrier gas is passed therethrough. Electronic pressure controller EPC-1 and control valves V4, V3, V2, V1, V5, and V6 are operated so that a portion of the carrier gas flows through the preconcentrator 104 and is vented from the system at vent AV1, and another portion of the carrier gas flows through the GC column 106 and the SAW detector. More specifically, a portion of the carrier gas from the supply 132 is passed through the PC manifold 116 to the preconcentrator 104. The carrier gas is passed through the preconcentrator 104, exits the preconcentrator 104 at the GC manifold 114, and passes through the GC manifold 114 via control valve V3. Flow through the preconcentrator 104 is countercurrent to the flow through the preconcentrator during the purging process. The carrier gas exiting the GC manifold 114 via control valve V3 passes through the sparger manifold 112 via control valves V2 and V1, and is vented from the system 100 via control valve AV1. Another portion of the carrier gas from supply 132 is passed through the GC manifold 114 via control valve V5. The carrier gas exiting the GC manifold via control valve V5 passes through the GC column 106 to the SAW detector 108 via control valve V6. In one embodiment, the electronic pressure controller EPC-1 regulates carrier gas flow to about 8 p.s.i. (55 kPa). The carrier gas flows across the SAW coating and further aids in the removal of moisture released from the SAW coating.

Figure 24:
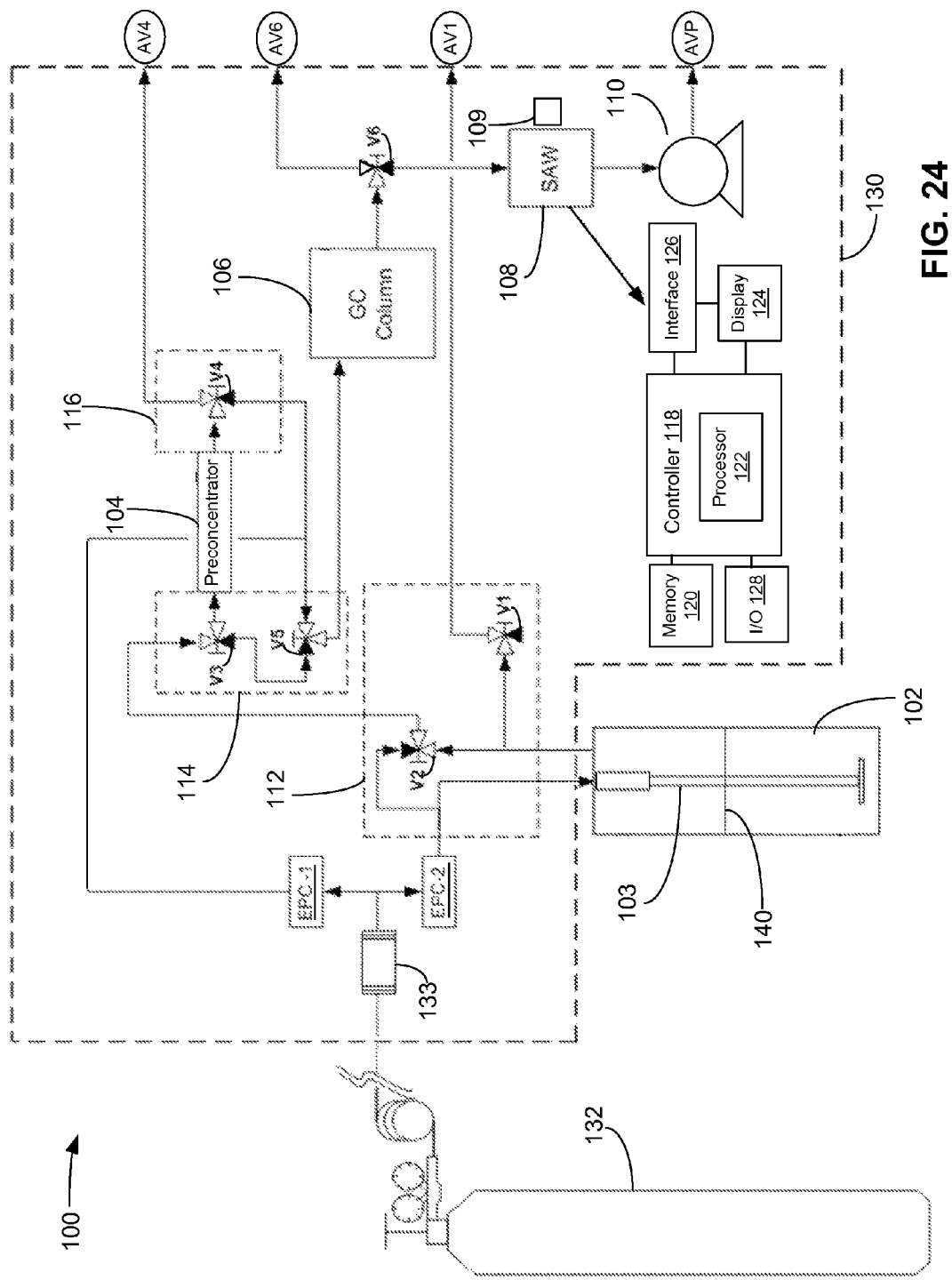
FIG. 24 is a schematic illustration of an exemplary chemical analysis system according to the invention in a third ventilation state.

At step 1024, the system is operated via the controller 118 to be in a third ventilation state and the system 100 undergoes a third ventilation process. The duration of the third ventilation process may range from about 0 seconds to about 20 seconds. In one embodiment, the third ventilation process is performed for about 10 seconds. FIG. 24 shows the system 100 in the third ventilation state. The electronic pressure controllers EPC-1 and EPC-2 are controlled via controller 118 such that there is no flow of carrier gas through the system 100. Control valve V1 is operated to provide a flow path from the sparger 103 and sample vessel 102 to vent AV1. Control valves V2, V3, and V4 are operated to provide a flow path from the sparger 103, sample vessel 102, and preconcentrator 104 to vent AV4. Control Valves V5 and V6 are operated to provide a flow path from the GC column 106 to vent AV 6.

Following the analytical process 1000, the system may be operated via the controller 118 to return to the standby state.

Although the invention has been shown and described with respect to a certain embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A system for detecting organic compounds in water including:
   a surface acoustic wave detector configured to detect a mass of organic compounds separated by a gas chromatograph column, the surface acoustic wave detector having a sensing surface with a coating;
   a vacuum pump for lowering pressure at the coating of the surface acoustic wave detector; and
   a controller configured to control operation of the vacuum pump to lower pressure at the coating of the surface acoustic wave detector to remove moisture from the coating.

2. A system according to claim 1, wherein the controller is further configured to cause carrier gas to flow from a carrier gas supply across the coating of the surface acoustic wave detector while the pressure at the coating is lowered.

3. A system according to claim 1, wherein the pressure at the coating is lowered without flow of carrier gas across the coating of the surface acoustic wave detector.

4. A system according to claim 1, wherein the controller is configured to control operation of the vacuum pump to lower the pressure at the coating of the surface acoustic wave detector to about the vapor pressure of water.

5. A system according to claim 1, wherein the pressure at the coating is lowered without application of heat at the coating.

6. A system according to claim 1, wherein controller is configured to control the operation of the vacuum pump after execution of a gas chromatography process in which the surface acoustic wave detector detects the mass of the organic compounds.

7. A system according to claim 1, further including:
   a sample vessel configured to contain a water sample from which the organic compounds are purged;
   a preconcentrator configured to collect the organic compounds; and
   a gas chromatograph column configured to separate the organic compounds as desorbed from the preconcentrator.

8. A system according to claim 7, wherein the controller is configured to control the operation of the vacuum pump after execution of a purging process in which the organic compounds are purged from the water sample and collected at the preconcentrator.

9. A method for detecting organic compounds in water including:
- purging the organic compounds from a water sample contained in a sample vessel;
- collecting the organic compounds with a preconcentrator;
- desorbing the organic compounds from the preconcentrator;
- separating the organic compounds as desorbed from the preconcentrator with a gas chromatograph column;
- detecting the mass of organic compounds separated by a gas chromatograph column with the acoustic wave detector; and
- lowering pressure at a coating of the surface acoustic wave detector to remove moisture from the coating.

10. A method according to claim 9, further including passing carrier gas across the coating of the surface acoustic wave detector while the pressure at the coating is lowered.

11. A method according to claim 9, wherein the pressure at the coating is lowered without passing carrier gas across the coating of the surface acoustic wave detector.

12. A method according to claim 9, wherein the pressure at the coating of the surface acoustic wave detector is lowered to about the vapor pressure of water.

13. A method according to claim 9, wherein the pressure at the coating is lowered without application of heat at the coating.

14. A method according to claim 9, wherein the pressure is lowered at the coating of the surface acoustic wave detector to remove moisture from the coating after the step of detecting the mass of the organic compounds.

15. A method according to claim 9, wherein the pressure is lowered at the coating of the surface acoustic wave detector to remove moisture from the coating during at least one of purging the organic compounds from the water sample or collecting the organic compounds with the preconcentrator.

* * * * *